United States Patent [19]
Stroebel et al.

[11] Patent Number: 5,725,561
[45] Date of Patent: Mar. 10, 1998

[54] METHOD AND APPARATUS FOR VARIABLE RATE CARDIAC STIMULATION

[75] Inventors: John C. Stroebel, Blaine; Michael F. Hess, Minneapolis; H. Toby Markowitz, Roseville, all of Minn.

[73] Assignee: Medtronic, Inc., Minneapolis, Minn.

[21] Appl. No.: 489,262

[22] Filed: Jun. 9, 1995

[51] Int. Cl.⁶ .................................................. A61N 1/362
[52] U.S. Cl. ........................................................ 607/9
[58] Field of Search ................................. 607/9, 17–19, 607/25

[56] References Cited

U.S. PATENT DOCUMENTS

| | | |
|---|---|---|
| 4,374,382 | 2/1983 | Markowitz . |
| 4,476,868 | 10/1984 | Thompson . |
| 4,485,813 | 12/1984 | Anderson et al. . |
| 4,556,063 | 12/1985 | Thompson et al. . |
| 4,562,841 | 1/1986 | Brockway et al. . |
| 4,587,970 | 5/1986 | Holley et al. . |
| 4,856,524 | 8/1989 | Baker, Jr. . |
| 5,005,574 | 4/1991 | Fearnot et al. ............ 607/21 |
| 5,052,388 | 10/1991 | Sivula et al. . |
| 5,127,404 | 7/1992 | Wyborny et al. . |
| 5,134,997 | 8/1992 | Bennett et al. ............ 607/18 |
| 5,144,949 | 9/1992 | Olson . |
| 5,271,395 | 12/1993 | Wahlstrand et al. . |
| 5,284,491 | 2/1994 | Sutton et al. ............ 607/17 |
| 5,292,340 | 3/1994 | Crosby et al. . |
| 5,417,716 | 5/1995 | Franberg et al. ............ 607/9 |
| 5,501,701 | 3/1996 | Markowitz et al. ............ 607/9 |

*Primary Examiner*—Jeffrey R. Jastrzab
*Attorney, Agent, or Firm*—Harold R. Patton; Michael B. Atlass

[57] ABSTRACT

A method and apparatus for variable rate cardiac stimulation, wherein sudden drops in the rate of delivery of stimulation pulses are avoided by means of rate smoothing and peak rate support functions. In one embodiment, circuitry in a cardiac pulse generator detects atrial events and maintains an updated value of the A-A time intervals between certain atrial events. If a preset ratio or total of these A-A intervals are found to have been shorter than the updated value by at a least a predetermined amount of time, a rate smoothing function is activated wherein the rate of delivery of stimulating pulses is prevented from changing, from cycle to cycle, by more than a predetermined maximum amount. A peak rate support function preferably employs the same updated value in the computation of "escape" intervals. Following the latest A-A interval, if that A-A interval is less than the updated value, then the updated value is used as the new escape interval. If the latest A-A interval is greater than or equal to the updated value but less than the previous updated value, the current escape interval is used as the new escape interval. If the latest A-A interval is less than both the previous updated value and the current updated value, the value updated is used as the new escape interval, and the pulse generator enters a decay mode wherein the escape interval is gradually and incrementally lengthened to prevent sudden changes in the rate of delivery of stimulation pulses.

21 Claims, 12 Drawing Sheets

METHOD AND APPARATUS FOR VARIABLE RATE CARDIAC STIMULATION

FIELD OF THE INVENTION

This invention relates generally to the field of automatic, body-implantable cardiac generators, and more particularly to a method and apparatus for performing cardiac stimulation at variable rates.

BACKGROUND OF THE INVENTION

In general, cardiac pulse generators are electrical devices used to supplant some or all of an abnormal heart's natural electrical function. Cardiac pacemakers typically operate to deliver appropriately timed electrical stimulation signals, sometimes called pacing pulses, designed to cause the myocardium to contract or "beat." Cardioverters, on the other hand, operate to more aggressively stimulate the heart, in order to terminate and/or prevent episodes of tachycardia, while cardiac defibrillators operate to deliver high energy pulses in order to terminate episodes of cardiac fibrillation.

For state-of-the-art pulse generators operating in a pacemaker mode, the rate at which stimulation signals are delivered may be variable. Such rate variation may occur automatically in response to detected changes in a patient's level of physical activity, or in response to detected changes in the patient's intrinsic cardiac rate. Variable-rate pulse generators often depend on physiologically-based signals, such as signals from sensors which measure naturally-occurring (intrinsic) cardiac electrical activity, or which measure the pressure inside the patient's ventricle. Such physiologically-based signals provide information regarding cardiac function and the need for pulse generator intervention, and thus are useful for determining a patient's metabolic demand for oxygenated blood.

One patient population for which physicians are currently exploring the use of pulse generators includes patients who suffer episodes of Vaso-Vagal Syncope (VVS). Such patients have fainting spells which are attributed to blood vessel dilation and inadequate cerebrovascular circulation. One accepted view of the phenomenon underlying VVS is that as the blood pools in the peripheral vessels, the body increases heart rate to compensate for the drop in cardiac output. A number of physiologic systems interpret the increased heart rate and small ventricular blood volumes as overwork and respond by slowing heart rate quickly, sometimes resulting in syncope (fainting).

Often, VVS patients exhibit wide fluctuations in heart rate just before a syncopal spell. Some current research suggests that these rate variations are the result of two competing feedback systems in the body acting together—one trying to slow heart rate, the other trying to increase cardiac output.

The solutions proposed by this invention lead to greater patient comfort (smoothed rate decline yields little symptomatic indicators to the patient) and enhanced mode switching. They can apply to any time the patient would otherwise experience rapid rate drops. By preventing rapid rate drops from occurring we can prevent patient anxiety, fatigue, and any other problem that may evolve from a rapid drop in rate.

SUMMARY OF THE INVENTION

In one aspect, the present invention relates to a method and apparatus adapted for pre-emptive treatment of potential VVS episodes. In a broader aspect, however, the present invention relates to a method and apparatus for computing the escape interval (pacing interval) for a variable rate cardiac pulse generator which function generally to "smooth" the pulse generator's response to sudden changes in intrinsic atrial rate.

In accordance with one aspect of the invention, the method and apparatus operate to pace the heart in accordance with a predetermined regimen intended to smooth out the wide cardiac rate variations exhibited by VVS patients prior to the onset of VVS.

In accordance with another aspect of the present invention, a cardiac pulse generator operates to implement a so-called "Peak Rate Support" algorithm which prevents steep drops in heart rate which would otherwise occur. In one embodiment, this is accomplished by pacing the heart at the intrinsic rate and then slowly reducing the rate to the "lower rate." In this regard, the patient preferably does not have an AV conduction disorder, (i.e., the patient does not depend on the pulse generator to provide ventricular stimulation). These patients, may, however, develop transient AV block, which may be treated with dual-chamber (e.g., DDD) pacing.

Peak Rate Support operation involves a simple algorithm which continuously maintains and updates a parameter called the "Average Atrial Interval" (AAI). In one embodiment of the invention, the AAI is adjusted at every atrial interval which ends in an intrinsic event or occurs between two paces—lower rate or sensor rate pacing, for example. The atrial intervals involved occur between Senses, Refractory Senses, and Paces. In a sinus tracking operation, where every atrial event is a Sense, each interval is used in adjusting the AAI. In a competitive pacing situation, where atrial pacing is closely coupled to intrinsic atrial activity, the Refractory Sense-Pace interval is not used in updating AAI, as it is not truly "Physiologic"—the pulse generator caused the interval, and thus the interval may or may not reflect the underlying intrinsic activity.

In accordance with another aspect of the present invention, updating the AAI value is a "biased delta" operation. That is, each adjustment modifies the AAI by a fixed amount (in milliseconds). If the atrial interval used for the calculation is smaller than the AAI, the AAI is reduced towards this interval a by a fixed amount (called "DELTADEC"). Likewise, if the Atrial interval is longer than the AAI, the AAI is increased by a different fixed amount (called "DELTAINC"). The AAI can never change in one step by more than these adjustment values. In one implementation the DELTADEC value is larger than the DELTAINC. This results in operation which tracks rapidly increasing atrial rates faster than decreasing atrial rates.

In accordance with yet another aspect of the present invention, Peak Rate Support can operate in one of two modes: "triggered" (or detection enabled), or an "always on" operation. The Triggered operation requires a detection criteria which screens precipitous drops in intrinsic rate. If Peak Rate Support operation is always on, no detection is necessary. If the Peak Rate Support is enabled by Detection, there is preferably provided a programmable time for the Peak Rate Support function to stay on. If Peak Rate Support is always on, this would not be relevant. Peak Rate Support is designed to work independently with any detection criteria desired.

The rate-smoothing capabilities of a pulse generator in accordance with the present invention allow the pulse generator to prevent large drops in pacing rate, even when erratic tracking of atrial electrical activity occurs. In addition to the Peak Rate Support functionality summarized above, the pulse generator in accordance with the present invention also is provided with a general rate-smoothing operation intended to work during normal DDD or DDDR pacing operation. The pulse generator may establish criteria for initiation of rate smoothing operation. When operating, rate smoothing maintains a pacing rate "floor." In accordance with one embodiment of the invention, the pacing rate is not allowed to drop below the aforementioned AAI minus a predetermined "Maximum Rate Drop" parameter. If the pacing rate drops to this level, the pacing rate is "smoothed" until it reaches the programmed lower rate (or sensor rate, for DDDR pulse generators).

Rate smoothing functionality for cardiac pacemakers has been suggested in the prior art (see, e.g., U.S. Pat. No. 4,562,841 to Brockway et al., entitled "Programmable, Multi-Mode Cardiac Pacemaker," and U.S. Pat. No. 4,856,524 to Baker, Jr., entitled "A-V Responsive Rate Adaptive Pacemaker"). It is believed, however, that the particular implementation of rate smoothing and Peak Rate Support functionality in a device in accordance with the present invention offers distinct advantages over the prior art, particularly with regard to the treatment of VVS patients. In one aspect, it is believed that the present invention is particularly well-suited to implementation in implantable devices operable to automatically switch between different pacing modes, and between pacing, cardioversion, and/or defibrillation modes.

BRIEF DESCRIPTION OF THE DRAWINGS

The foregoing and other aspects of the present invention can be more completely understood with reference to a detailed description of a specific embodiment of the invention, when read in conjunction with the accompanying drawings, wherein.

DETAILED DESCRIPTION OF A SPECIFIC EMBODIMENT OF THE INVENTION

General Description

Figure 1:
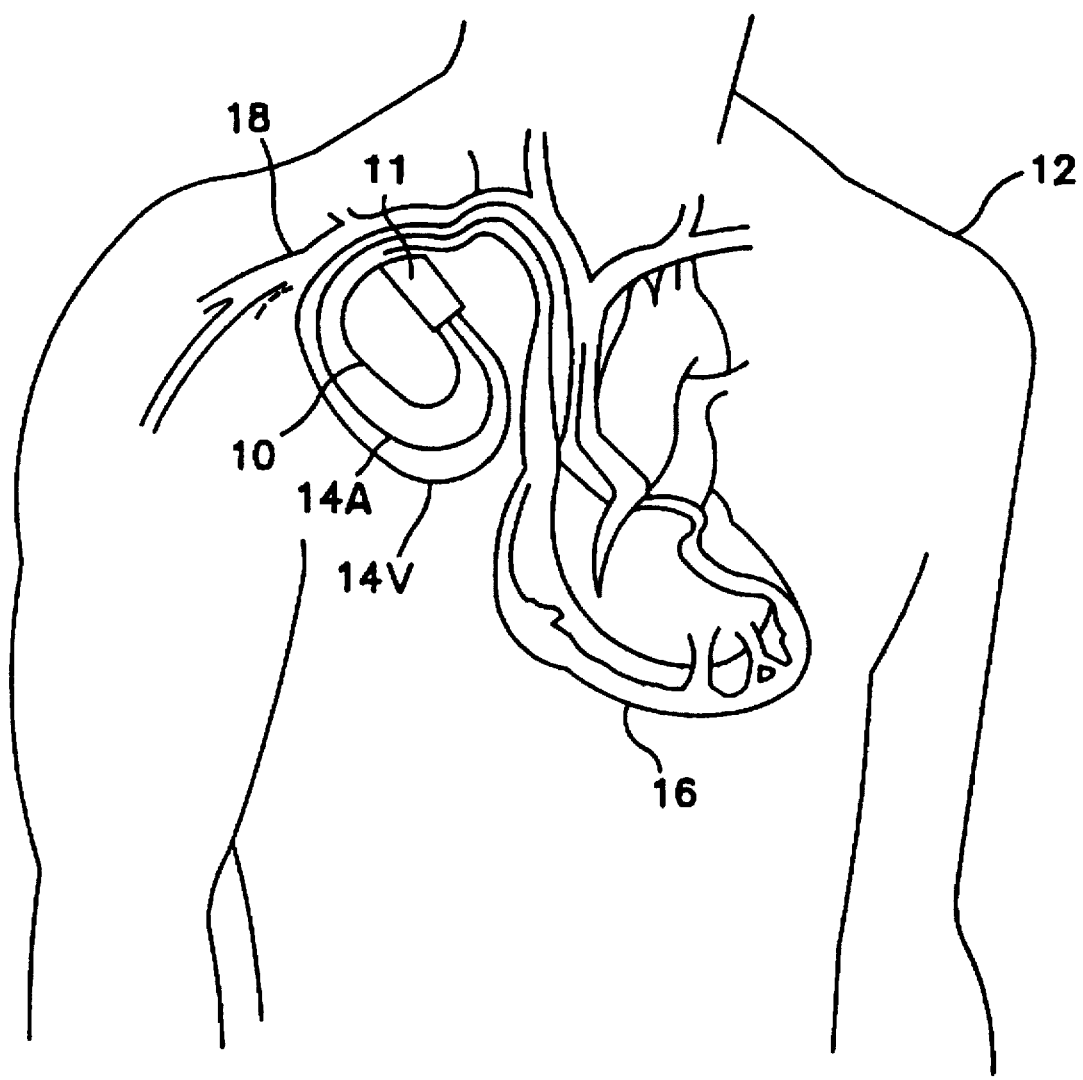
FIG. 1 is an illustration of a cardiac pulse generator in accordance with one embodiment of the present invention having been implanted into a patient.

Referring to FIG. 1, there is shown an illustration of generally where a pulse generator 10 in accordance with one embodiment of the invention may be implanted in a patient 12. As will hereinafter be described in further detail, it is contemplated that pulse generator 10 in the presently disclosed embodiment of the invention may be a multi-mode device capable of operating in several therapeutic modes, for example pacing, cardioversion, and defibrillation. Depending upon the capabilities of the implanted device with which the present invention is practiced, the implant site may be different than what is illustrated in FIG. 1. Modem combination pacemaker/cardioverter/defibrillators ("PCDs"), for example, are often implanted at an abdominal implant site.

In accordance with conventional practice in the art, pulse generator 10 is housed within a hermetically sealed, biologically inert outer canister, which may itself be conductive and thus serve as an indifferent electrode in the pulse generator's stimulating/sensing circuit. One or more implantable leads, collectively identified with reference numerals 14V (ventricular) and 14A (atrial) in FIG. 1, are electrically coupled to pulse generator 10 in a conventional manner, extending into the patient's heart 16 via a vein 18. Disposed generally near the distal end of leads 14a and 14b are one or more exposed conductive electrodes for receiving electrical cardiac signals and/or for delivering electrical stimuli to heart 16.

Figure 2:
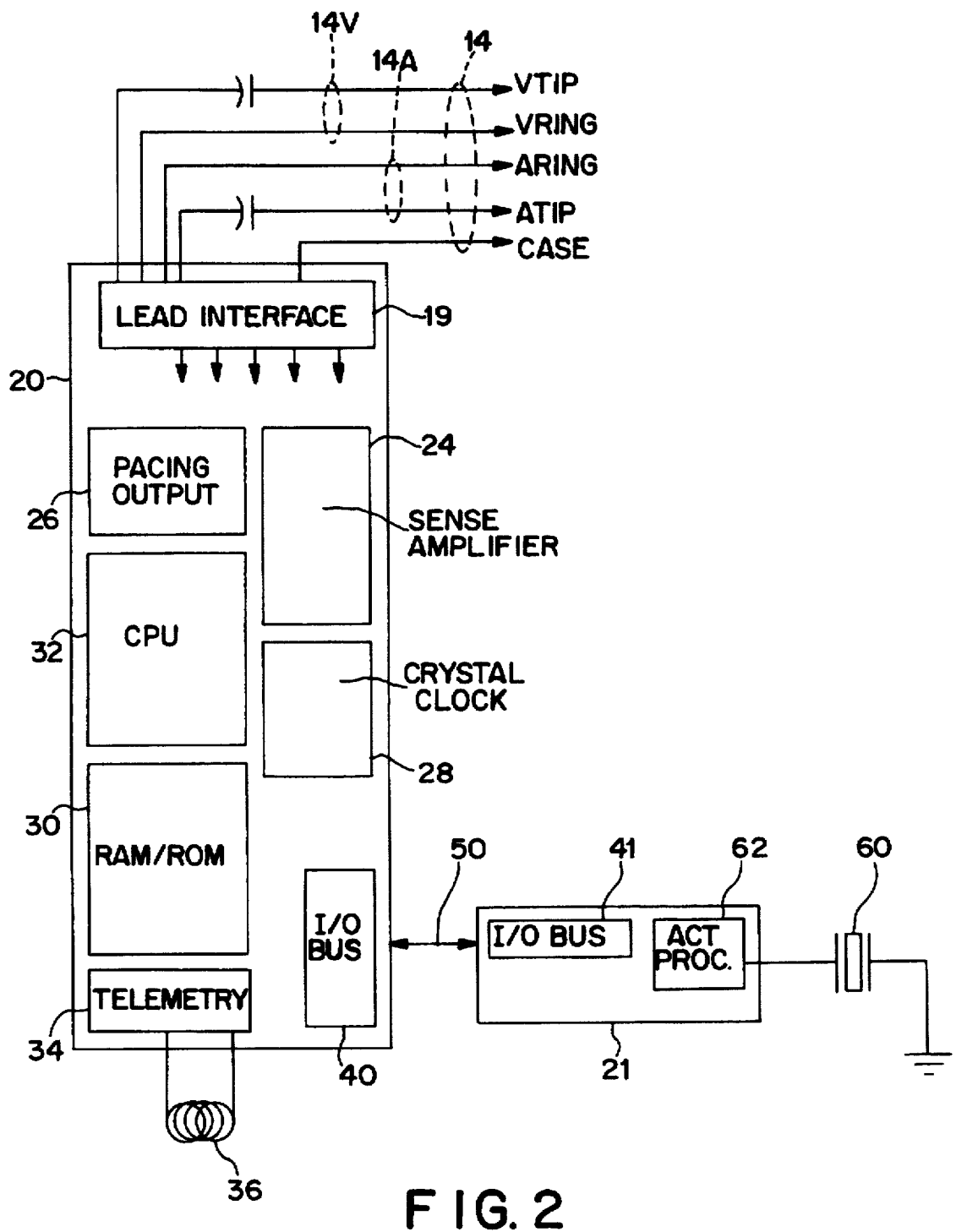
FIG. 2 is a block diagram showing the functional components of the pulse generator from FIG. 1.

Turning now to FIG. 2, there is shown a block diagram of the electronic circuitry which makes up pulse generator 10 in accordance with the presently disclosed embodiment of the invention. As can be seen from FIG. 2, pulse generator 10 comprises a primary stimulation control circuit 20, and an activity sensor circuit. Much of the circuitry associated with stimulation control circuit 20 is of conventional design, in accordance, for example, with what is disclosed in U.S. Pat. No. 5,052,388 to Sivula et al, entitled "Method and Apparatus for Implementing Activity Sensing in a Pulse Generator." Numerous other methods can be adapted based on motion detecting, respiration, posture, and so forth as is well known to those in this art for detection and measuring patient activity. To incorporate such methods or other apparatus as sensors appropriate conventional modification should be made. The Sivula et al. '388 patent is hereby incorporated by reference herein. To the extent that certain components of pulse generator 10 are conventional in their design and operation, such components will not be described herein in detail, as it is believed that design and implementation of such components would be a matter of routine to those of ordinary skill in the art. For example, stimulation control circuit 20 in FIG. 2 includes sense amplifier circuitry 24, stimulating pulse output circuitry 26, a crystal clock 28, a random-access memory and read-only memory (RAM/ROM) unit 30, a central processing unit (CPU) 32, and a telemetry circuit 34, all of which are well-known in the art.

Pulse generator 10 preferably includes internal telemetry circuit 34 so that it is capable of being programmed by means of external programmer/control unit 17 (not shown in the Figures). Programmers and telemetry systems suitable for use in the practice of the present invention have been well known for many years.

Known programmers typically communicate with an implanted device via a bidirectional radio-frequency telemetry link, so that the programmer can transmit control commands and operational parameter values to be received by the implanted device, and so that the implanted device can communicate diagnostic and operational data to the programmer. Programmers believed to be suitable for the purposes of practicing the present invention include the Model 9760 and Model 9790 Programmers, commercially-available from Medtronic, Inc., Minneapolis, Minn.

Various telemetry systems for providing the necessary communications channels between an external programming unit and an implanted device have been developed and are well-known in the art. Telemetry systems believed to be suitable for the purposes of practicing the present invention are disclosed, for example, in the following U.S. Patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device". The Wyborny et al. '404, Markowitz '382, and Thompson et al. '063 patents are commonly assigned to the assignee of the present invention, and are each hereby incorporated by reference herein in their respective entireties.

Typically, telemetry systems such as those described in the above-referenced patents are employed in conjunction with an external programming/processing unit. One programmer for non-invasively programming a cardiac pulse generator is described in the above-referenced Medtronic 9760 or 9790 programmers.

Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna for receiving downlink telemetry signals and for radiating RF signals for uplink telemetry. The system is modeled as an air-core coupled transformer. An example of such a telemetry system is shown in the above-referenced Thompson et al. '063 patent.

In order to communicate digital data using RF telemetry, a digital encoding scheme such as is described in the above-reference Wyborny et al. '404 patent can be used. In particular, for downlink telemetry a pulse interval modulation scheme may be employed, wherein the external programmer transmits a series of short RF "bursts" or pulses in which the interval between successive pulses (e.g., the interval from the trailing edge of one pulse to the trailing edge of the next) is modulated according to the data to be transmitted. For example, a shorter interval may encodes a digital "0" bit while a longer interval encodes a digital "1" bit.

For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen position data frame may be defined, wherein a pulse in one of the time slots represents a unique four bit portion of data.

Programming traits such as the above-referenced Medtronic Model 9760 and 9790 programmers typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

With continued reference to FIG. 2, pulse generator 10 is coupled to leads 14A and 14V which, when implanted, extend transvenously between the implant site of pulse generator 10 and the patient's heart 16, as previously noted with reference to FIG. 1. Physically, the connections between leads 14A and 14V and the various internal components of pulse generator 10 is facilitated by means of a conventional connector block assembly 11, shown in FIG. 1 but not shown in FIG. 2. Electrically, the coupling of the conductors of leads and internal electrical components of pulse generator 10 is facilitated by means of a lead interface circuit 19 which functions, in a multiplexer-like manner, to selectively and dynamically establish necessary connections between conductors in leads 14A and 14V and individual electrical components of pulse generator 10, as would be familiar to those of ordinary skill in the art. For the sake of clarity, the specific connections between leads 14 and the various components of pulse generator 10 are not shown in FIG. 2, although it will be clear to those of ordinary skill in the art that, for example, leads 14 will necessarily be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14.

In the presently disclosed embodiment, two leads are employed—an atrial lead 14A having atrial tip and ring electrodes (ATIP and ARING in FIG. 2), and a ventricular lead 14V having ventricular tip and ring electrodes (VTIP and VRING in FIG. 2). In addition, as noted above, the conductive hermetic canister of pulse generator 10 serves as an indifferent electrode (CASE in FIG. 2).

As previously noted, stimulation control circuit 20 includes central processing unit 32 which may be an off-the-shelf programmable microprocessor or microcontroller, but in the presently preferred embodiment of the invention is a custom integrated circuit. Although specific connections between CPU 32 and other components of stimulation control circuit 20 are not shown in FIG. 2, it will be apparent to those of ordinary skill in the art that CPU 32 functions to control the timed operation of stimulating pulse output circuit 26 and sense amplifier circuit 24 under control of programming stored in RAM/ROM unit 30. It is believed that those of ordinary skill in the art will be familiar with such an operative arrangement.

With continued reference to FIG. 2, crystal oscillator circuit 28, in the presently preferred embodiment a 32,768-Hz crystal controlled oscillator, provides main timing clock signals to stimulation control circuit 20. Again, the lines over which such clocking signals are provided to the various timed components of pulse generator 10 (e.g., microprocessor 32) are omitted from FIG. 2 for the sake of clarity.

It is to be understood that the various components of pulse generator 10 depicted in FIG. 2 are powered by means of a battery (not shown) which is contained within the hermetic enclosure of pulse generator 10, in accordance with common practice in the art. For the sake of clarity in the Figures, the battery and the connections between it and the other components of pulse generator 10 are not shown.

Stimulating pulse output circuit 26, which functions to generate cardiac stimuli under control of signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits which would be suitable for the purposes of practicing the present invention.

Sense amplifier circuit 24, which is of conventional design, functions to receive electrical cardiac signals from leads 14A and 14V, and to process such signals to derive event signals reflecting the occurrence of specific cardiac electrical events, including atrial contractions (P-waves) and ventricular contractions (R-waves). These event-indicating signals are provided to CPU 32 for use by CPU in controlling the synchronous stimulating operations of pulse generator 10 in accordance with common practice in the art.

Activity circuit 21 is also of conventional design, as exemplified by U.S. Pat. No. 4,485,813 to Anderson et al., U.S. Pat. No. 5,271,395 to Wahlstrand et al. entitled "Method and Apparatus for Rate-Responsive Cardiac Pacing," (which patents are hereby incorporated by reference in their entirety) or by the above-referenced Sivula '388 patent. Associated with activity circuit 21 is a microphone-like piezoelectric crystal element 60, which functions to provide a raw sensor signal to activity circuit 21 reflecting the level of a patient's physical activity. (If other sensors were used the circuit optimum form of circuit 21 would be different, perhaps allowing for multiple weighted inputs from multiple sensors for example 18 preferred) The raw sensor signal from piezoelectric element 60 is processed by an activity processing circuit 62 to derive a sensor signal which, in either analog or digital form, reflects the patient's physical activity level and thus the patient's metabolic demand for oxygenated blood. The sensor signal is communicated, via an I/O bus 50, to stimulation control circuit 20, for use by CPU 32 in controlling pulse generator 10 to perform activity-responsive pacing. (Associated with stimulation control circuit 20, and with activity circuit 21, are I/O bus interface circuits 40 and 41, respectively, which function to coordinate transfers of digital and/or analog information between stimulation control circuit 20 and activity circuit 21, in a conventional manner.)

Description of Rate Smoothing Operation

As noted in the Summary of the Invention section above, pulse generator 10 in accordance with the presently disclosed embodiment of the invention is provided with a rate smoothing capability to prevent large, sudden drops in pacing rate due, for example, to erratic tracking of atrial electrical activity. Clinical needs for this capability include: transient sino-atrial block, intermittent loss of atrial sensing, smoothing of ventricular rate during Wenckebach operation, especially during tacharrhythmias, and prevention of precipitous rate drops in patients with Sick Sinus Syndrome, or Brady/Tachy syndrome.

In general it is considered symptomatic for a patient to experience sudden rate drops so we smooth them. The contrary, sudden rate increase, does not appear to require smoothing. In support of its rate smoothing functionality, the preferred embodiment pulse generator 10, and specifically, CPU 32, maintains a plurality of numeric values in memory unit 30, these values being periodically updated to determine whether and how to apply rate smoothing.

One such value, which for convenience we call the "Average Atrial Interval" ("AAI" although it need not be but could be a mathematical "average"), is adjusted by CPU 32 following every atrial interval which ends in an intrinsic (atrial non-paced) event and those intervals between two atrial paced events. This AAI is calculated based on the measure of time between these two atrial paced events or an atrial sense event followed by a sensed or paced atrial event but not those event pairs where an atrial sensed event is followed by an atrial paced event. In other words the atrial (A-A) intervals for which the AAI is updated occur between Senses, Refractory Senses, and Paces of the atrium. In a sinus tracking situation, where every atrial event is a sensed (intrinsic) event, each A-A interval would be used in adjusting the AAI. In a competitive pacing situation, where atrial pacing is closely coupled to intrinsic atrial activity, the Refractory Sense-Pace interval is not used as it may not actually reflect underlying intrinsic activity.

In the presently preferred embodiment, updating the AAI is a "biased delta" operation. Each adjustment modifies the AAI by a fixed amount. If the A-A interval used for an update of the AAI is smaller than or equal to the current AAI, the AAI is reduced by a fixed amount, called DELTADEC. Likewise, if the A-A interval used for an update of the AAI is larger than the current AAI, the AAI is increased by a different fixed amount, DELTAINC. DELTADEC and DELTAINC are included among the programmable values that may be selected and modified by a physician. Such modification is done using the pulse generator's telemetry programming facilities, as is a well-known practice in the art.

For any given update, the AAI can never change by more than the DELTADEC or DELTAINC values. In the presently preferred implementation of the invention, DELTADEC is larger than DELTAINC. This results in a rate-smoothing algorithm that tracks rapidly increasing atrial rates faster than decreasing atrial rates.

One result of the step-wise incrementing and decrementing of the AAI is that it is possible for the AAI to overshoot the intrinsic atrial rate. For example, if it is assumed (1) that a current AAI value is 600-mSec (milliseconds); (2) that the programmed DELTADEC value is 24-mSec; (3) that the programmed DELTAINC value is 8-mSec; (3) that an atrial sense occurs 550-mSec following a prior atrial sense (i.e., an atrial interval of 550-mSec), resulting in an updated AAI value of 576-mSec (600–24); and (4) that the next intrinsic atrial event occurs 560-mSec following the one for which the AAI was updated to 576-mSec. In this situation, the next AAI update would again entail decrementing the current AAI by 24-mSec. This adjustment, however, would result in an AAI of 552, slightly smaller than the intrinsic A-A interval (560-mSec) just measured. If the next intrinsic atrial event is in 560-mSec from the last one, DELTA INC. will be added to 552 yielding a new AAI of 560-mSec.

The other two values in our preferred embodiment for affecting rate smoothing are related through a matrix we call Count N, containing N values of P total values we call Count P. Count P is either on/off, true/false, one/zero, etc. and the number in the matrix or list of Count P variables that make up the set Count N we say is P in length. The total of those variables Count P that are indicative of a satisfied or recordable condition are called N. So, for example if we have for the last six cardiac cycles found the condition in five measured intervals sated (i.e., the time interval is less than the AAI minus the interval indicative of maximum rate drop) four times, the string of Count P's would be Count P 1–5, and have values like {1,0,1,1,1}. Thus, we would say N of P=4 of 5, since 4 times out of 5 cycles that were readable the condition was such that the time from event to event was less than the AAI minus the Max Rate Drop value (i.e., zero was stored in Count N for four Count P values out of five total CountP values).

It should be apparent by now that the Maximum Rate Drop value is set to prevent abrupt downward adjustments in rate.

One purpose in defining the N-of-P rate smoothing criteria is to enable the programming physician or clinician to control how much of a role Rate Smoothing will play in controlling the pacing rate. Selecting a low Rate Smoothing Threshold (like 1 of 5) will cause Rate Smoothing to be easily triggered and continually smooth the pacing rate, whereas selecting a high Rate Smoothing Threshold (say, 4 of 5 for example) will cause Rate Smoothing to be triggered only when atrial rate increases rapidly, such that only the rate of atrial tachyarrhythmias will be smoothed.

If preferred the rate smoothing function of pulse generator 10 can maintain a pacing rate "floor" when the pulse generator is operating in pacing mode. The pacing rate in this embodiment will not be allowed to drop below the average atrial rate (i.e., the pacing interval will not exceed the AAI minus a predetermined value such as the Maximum Rate Drop). If the pacing rate drops to this point, it will be smoothed in accordance with a predetermined deceleration or decay function, until it reaches the programmed lower rate (or the so-called Sensor Rate, for rate-responsive pulse generators operating in a DDDR pacing mode).

Rate smoothing for pulse generator 10 can be reset to smoothing from a higher rate after it has been activated if the N of P criteria described above are satisfied. During rate smoothing, the N in N of P is only incremented if the pacing interval becomes greater than the AAI plus the Rate Smoothing Threshold, and the pulse generator is tracking intrinsic atrial activity.

The decision to activate rate smoothing is always activated following ventricular events. Thus, rate smoothing can only be activated following an A-V interval, or following a truncated A-V interval if ventricular inhibition occurs.

For rate-responsive pulse generators having the capability to pace at a "sensor interval" (i.e., at a rate whose pacing interval is determined as a function of a sensor, such as activity sensor 60, which reflects a patient's metabolic demand), and for DDD pacing using the programmed "lower rate" a special V-A interval, called the VASmooth interval, is started following an A-V interval. The VASmooth interval is equal to the last measured V-V interval minus the last A-V interval plus a predetermined Maximum Rate Drop value, to be hereinafter described in further detail. If the sensor interval is less than or equal to the last measured V-V interval, sensor rate (i.e., faster than intrinsic) pacing will be delivered to the heart. However, if the sensor interval is greater than the last measured V-V interval, the escape rate (the interval between paces) will decay in accordance with a predetermined deceleration or decay function, such as that described in the above-referenced Sivula et al. '388 patent, until the escape rate is greater than or equal to the programmed lower rate (or the current sensor rate, for rate-responsive pulse generators in DDDR mode).

In the presently preferred embodiment of the invention, the rate smoothing decay parameter is programmable in the range from 10-sec to 2.5-min. The rate smoothing decay function in the preferred embodiment is similar to or uses the sensor rate deceleration function disclosed in the above-referenced Sivula et al. '388 patent. The value of the rate smoothing decay parameter in this embodiment represents the time interval required for the pulse generator to change from the current pacing interval to 90% of the desired pacing interval (e.g., lower rate limit interval or Sensor Rate interval).

Although numerous deceleration or decay formulas are known and could be used and easily devised, in general some can be explained to work by picking a small fixed interval and adding it to the current interval to come up with the next interval until the lower rate (expressed as a target interval) is reached. Making this small interval larger increases the rate decay, making it smaller causes the drop to decay more slowly.

During rate smoothing operation, if a pacing cycle is started with a sensed atrial event and an A-V interval, the V-A interval following that A-V interval can be extended only by an amount that corresponds to a programmable drop in pacing rate called Maximum Rate Drop. In one embodiment, to save computation time and energy, a look-up table is maintained in memory unit 30 to determine what the V-A interval must be increased by to drop the pacing rate by Maximum Rate Drop. The table is preferably constructed so that the longer the current interval, the larger the increment that may be added to it. Deceleration of the pacing interval is resumed from this new rate that adds the new increment to the current interval. This promotes proper tracking of sinus rates, yet provides adequate pacing support when the atrial rate drops abruptly. If desired, a formula and processor combination could be used instead of a table but that is not currently preferred.

Figure 3:
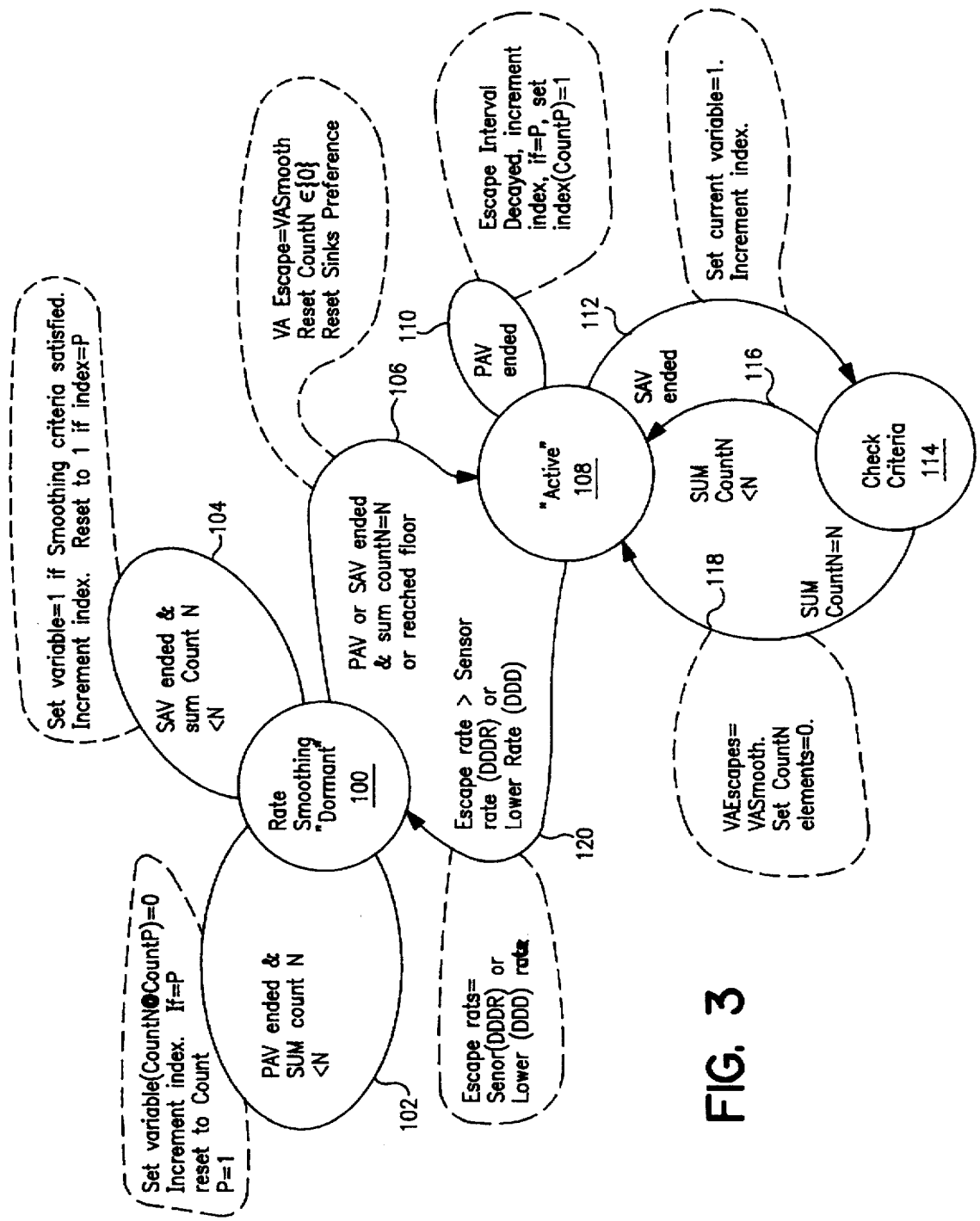
FIG. 3 is a state diagram illustrating the operation of the pulse generator from FIG. 1 in performing a rate smoothing function.

Turning now to FIG. 3, there is shown a state diagram illustrating operation of the rate smoothing function in the preferred embodiment pulse generator 10. Regarding the N of P criterion for activation of rate smoothing, this function is preferably handled in memory unit 30, by storing a one-dimensional array "CountN" (such that it contains elements [1 ... P]), an index to these elements, "CountP", and a counter, "N". Initially, each element in the array CountN is set to zero, and the CountP index value is set to one (1). For each atrial cycle, the index (CountP) is incremented by one and the next element in CountN is pointed to. If, for a given atrial cycle that meets the criterion for and AAI update as set forth above, the A-A interval is found to be less than the current AAI value by at least the Rate Smoothing Threshold value, the CountN array element value at "CountP" is "set" (preferably to "1"). As will be appreciated this scheme enables the N of P determination to be made by simply summing all of the elements "set" or valued at 1 (of all the P elements) in the CountN array.

As noted previously, rate smoothing is only activated upon a determination that the N of P rate smoothing criteria have been met. (In the current preferred implementation this means the sum of all values of CountN>N.) Thus, during normal operation, the rate smoothing function is dormant. This dormant state is represented by state node 100 in FIG. 3.

A first state transition, (shown as a loop and designated with reference numeral) 102 in FIG. 3, reflects a situation wherein pulse generator 10, with its rate smoothing function dormant, detects a "PAV" (i.e., a ventricular event following a paced atrial event) and wherein the sum of the variable values of CountN is less than N. As shown in FIG. 3, state transition 102 begins and ends in the dormant state. When state transition 102 is taken the variable indexed by CountP is set to zero and the index to the next variable to be evaluated is incremented (or reset to 1 if CountP=P).

State transition 104 in FIG. 3 is similar to transition 102, but occurs after an "SAV" (i.e., a ventricular event following a sensed atrial event), if the sum of the values of CountP is less than N. When transition 104 is taken the current variable indexed by CountP is set to one if the N-of-P criteria is satisfied by the latest A-A interval and CountP is incremented (or reset to one if CountP=P).

If either an SAV or a PAV occurs and the sum of variable values=N, then state transition 106 is taken from dormant state 100 to active state 108. When transition 106 is taken, the pulse generator's V-A escape interval (i.e., the interval between a ventricular event and the delivery of a subsequent atrial pace in the absence of sensed atrial activity) is set to the VASmooth value previously described. Additional actions associated with state transition 106 include resetting all the CountN array variable values to zero and CountP index to one.

In state 108, when a PAV occurs, the value of variable CountN (at index CountP) is set to zero and CountP is incremented (or reset to one if equal to P). In addition, the (A-A) escape interval is decayed by a predetermined amount, in accordance with the pulse generator's deceleration function, as previously discussed. This is reflected in state transition 110 in FIG. 3. On the other hand, when an SAV occurs when pulse generator 10 is in state 108, the V-A escape interval is set to the VASmooth value, the value of the variable CountN [CountP] is set to one, and CountP is incremented, as represented by state transition 112 from state 108 to state 114.

In state 114, the N of P rate smoothing criteria are checked. If the sum of values of CountN is less than N, pulse generator 10 returns to active state 108 (transition 116). However, if equal to N, transition 118 to state 108 is taken, the V-A escape interval is set to VASmooth, and the CountN array of values is reset to zero.

When rate smoothing is active (state 108), the pulse generator's escape rate (i.e., its A-A pacing interval) is compared with the currently programmed lower rate limit interval (for DDD pacing) or with the current sensor interval (for DDDR pacing). If the escape interval is greater than or equal to the programmed lower rate limit interval (DDD pacing) or sensor rate (DDDR pacing), transition 120 to dormant state 100 is taken. This prevents pulse generator 10 from pacing at a rate lower than the programmed lower rate limit interval (or lower than the sensor interval, for DDDR pacing). When transition 120 is taken, the pulse generator's escape interval is set to the programmed lower rate limit interval (or sensor interval, for DDDR pacing).

Figure 4:
FIG. 4 is a plot of pulse generator and cardiac electrical activity illustrating the effect of the rate smoothing function on the operation of the pulse generator from FIG. 1.
Figure 4:
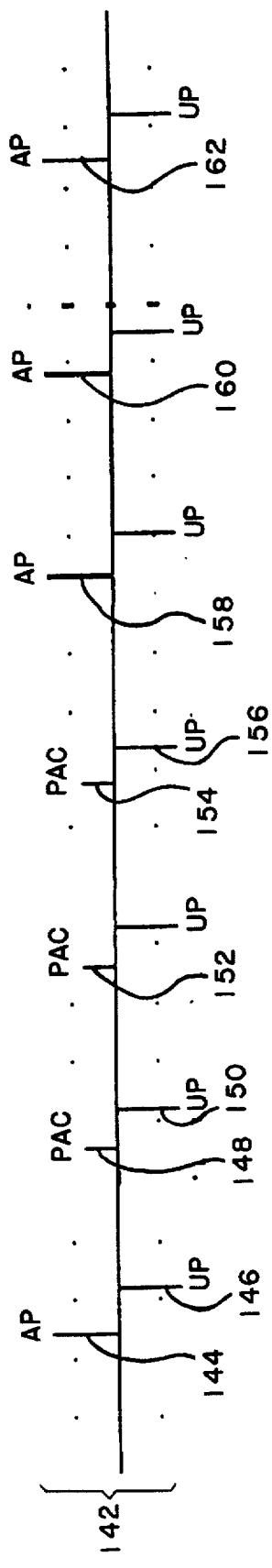

Referring to FIG. 4, there is shown a strip-chart illustrating an example of rate smoothing performed by pulse generator 10 in accordance with the presently preferred embodiment of the invention. In FIG. 4, a patient's cardiac electrical waveform is designated with reference numeral 140. An event marker channel, such as of the kind described in the above-referenced Markowitz '382 patent, is designated with reference numeral 142.

The cardiac and pulse generator activity represented in FIG. 4 begins with an atrial paced event 144, followed by a ventricular paced event 146. Next, a premature atrial contraction (PAC) 148 is detected. In this example, atrial contraction 148 is deemed premature because it occurred prior to the expiration of a time period corresponding to the time interval (AAI minus Rate Smoothing Threshold) following the previous atrial event. 144. Following PAC 148 is a ventricular pace 150.

Similarly, a second PAC 152, and a third PAC 154, are detected. For the example of FIG. 4, the N of P rate smoothing activation criteria are defined as N=3 and P=4. Thus, upon detection of PAC 154, the N of P criteria are fulfilled, and the pulse generator's rate smoothing function is activated, once ventricular event 156 occurs (recall that all decisions to activate rate smoothing are made following ventricular events). As noted above, the rate smoothing function involves establishing a pacing rate "floor", such that the pacing rate is prevented from dropping below the rate corresponding to the AAI minus the predetermined Maximum Rate Drop value. To this end, during rate smoothing operation, if a pacing cycle is started with a sensed atrial event and a subsequent A-V interval, the V-A interval which follows is extended to ensure that the pacing cycle lasts for an interval corresponding to AAI minus Maximum Rate Drop. As also previously described, the mount by which the V-A interval must be extended to ensure this, is preferably obtained by reference to a look-up table maintained in memory unit 30.

Thus, with reference to FIG. 4, it can be seen that as a result of premature atrial contraction 154 and the subsequent activation of the rate smoothing function, the interval between sensing atrial event 154 and the delivery of another atrial pacing pulse 158 is extended to be at the AAI minus Maximum Rate Drop value. In FIG. 4, atrial pacing pulses 158, 160 and 162 all exhibit rate smoothing.

Figure 5:
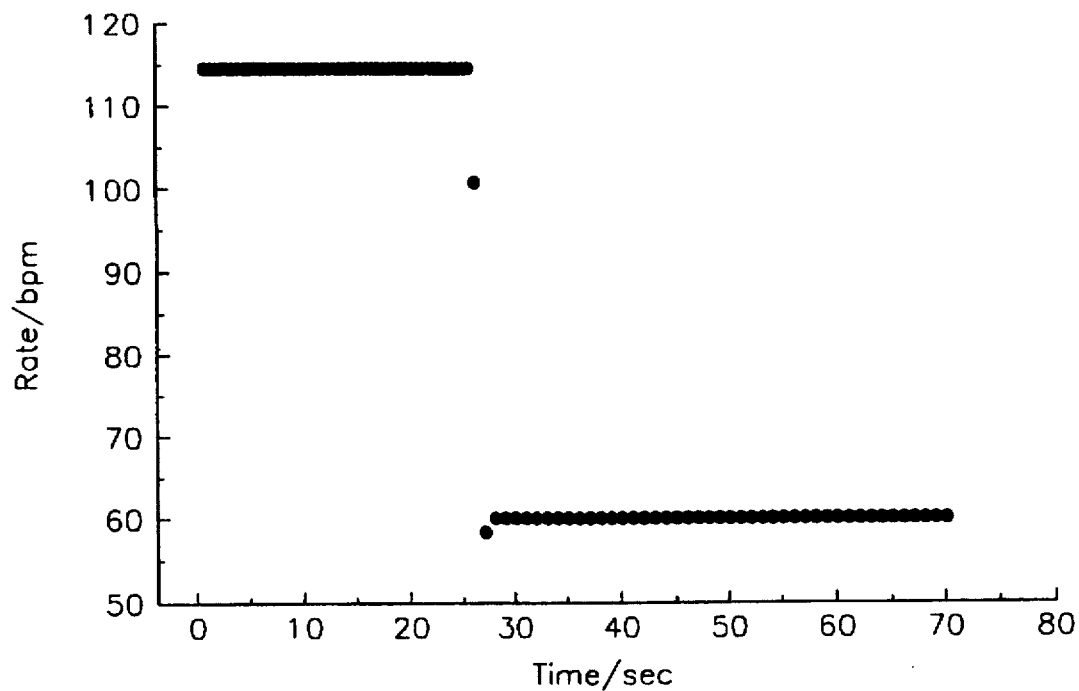
FIG. 5 is a plot showing a prior art pulse generator's response to a precipitous drop in intrinsic atrial activity.
Figure 6:
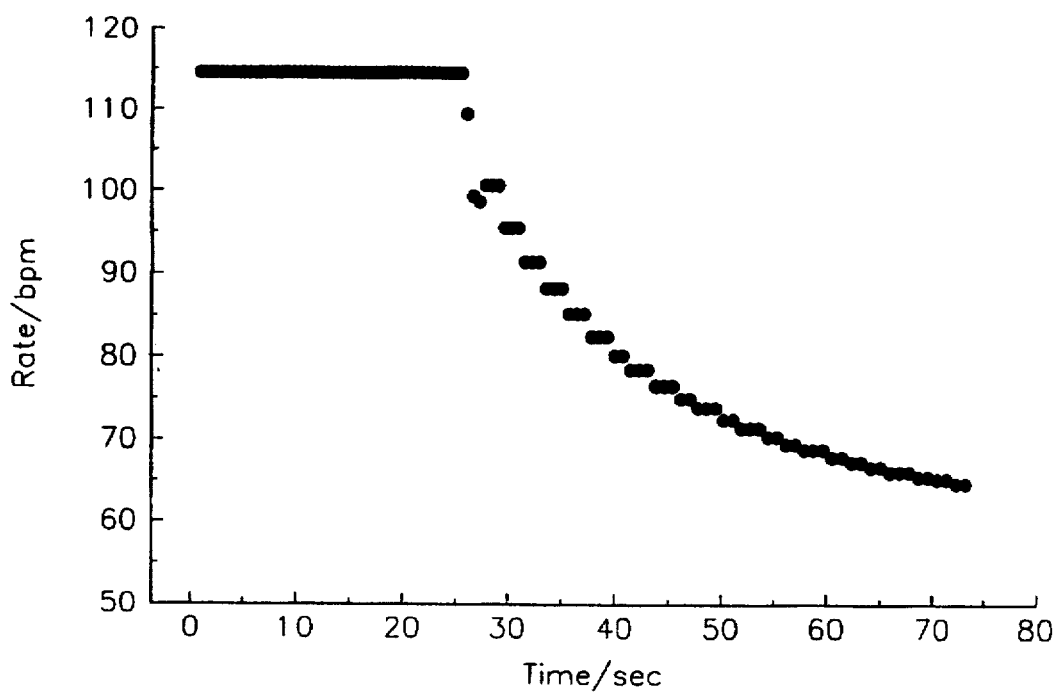
FIG. 6 is a plot showing the response of the pulse generator from FIG. 1 to a precipitous drop in intrinsic atrial activity.

The effects of rate smoothing operation in accordance with the presently disclosed embodiment of the invention may be better appreciated with reference to specific examples of cardiac conditions for which rate smoothing is desirable. In FIG. 5, there is shown an example of a prior art (i.e., non-rate smoothing) pulse generator's response to a precipitous drop in tracked atrial activity, caused, for example, by transient sino-atrial (SA) block, sick sinus syndrome, brady-tachy sinus syndrome, chronotropic incompetence, persistent sinus bradycardia, sinus arrest or the like. With no rate smoothing, the drop in atrial rate causes a corresponding drop in pacing rate, as shown in FIG. 5. In FIG. 6, on the other hand, the rate-smoothed response of pulse generator 10 in accordance with the presently disclosed embodiment of the invention to the same drop in tracked atrial rate exhibits a much more gradual decline in pacing rate. As shown in FIG. 6, pulse generator 10 tracks the atrial rate until the sharp drop occurs, at which point the rate smoothing operation described above results in gradual deceleration of the pacing rate down to the lower rate limit interval or sensor interval, whichever applies.

Figure 8:
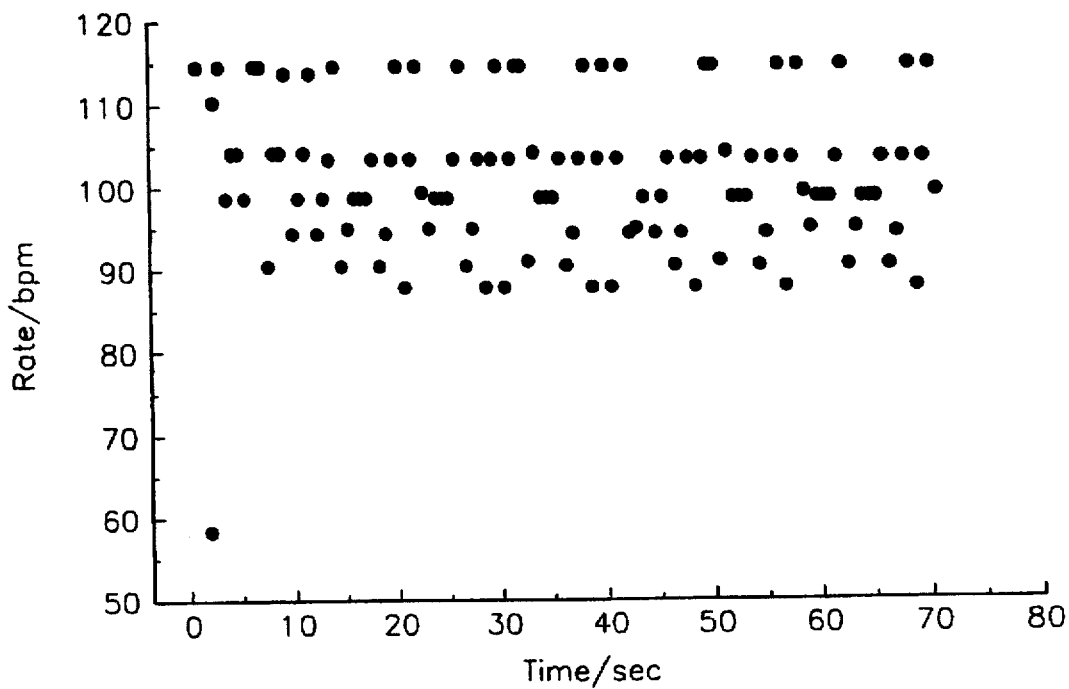
FIG. 8 is a plot showing the response of the pulse generator from FIG. 1 to intermittent atrial undersensing.
Figure 7:
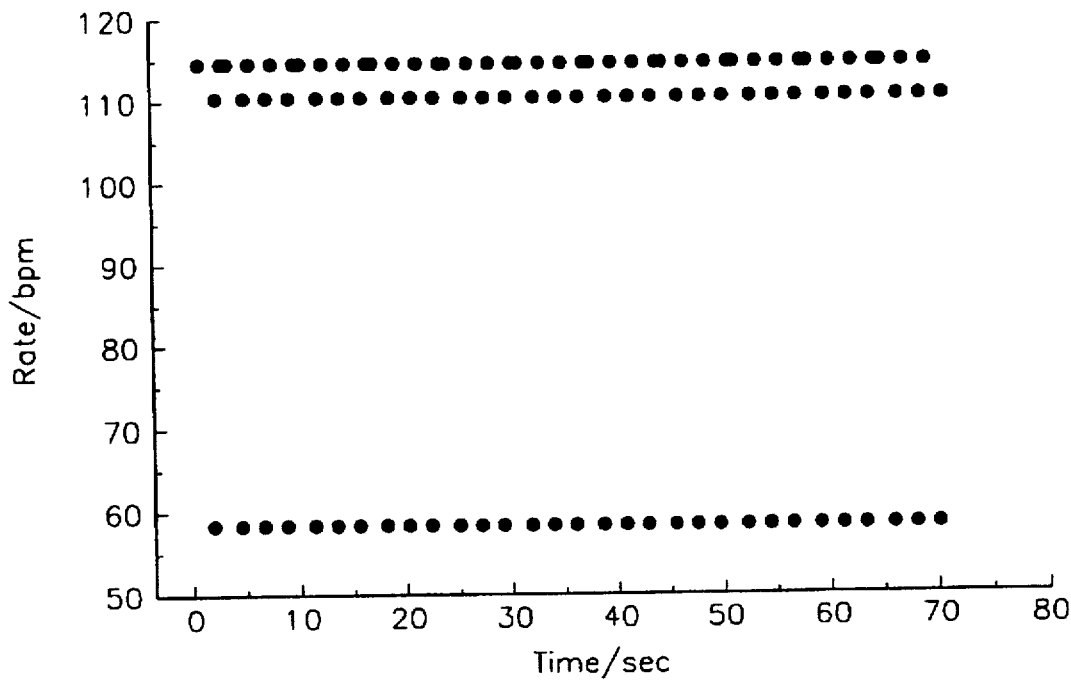
FIG. 7 is a plot showing the response of a prior art pulse generator to intermittent atrial undersensing.

In FIG. 7, there is shown a plot of a prior art pulse generator's response to intermittent loss of atrial sensing. As shown in FIG. 7, the prior art pulse generator's response is to intermittently pace at its lower rate limit (or sensor interval, in DDDR pulse generators) whenever an atrial beat fails to be sensed. In FIG. 8, on the other hand, the rate smoothing function of pulse generator 10 in accordance with the presently disclosed embodiment of the invention enables it to exhibit a response in which the band of ventricular rate variations is narrowed from nearly 60-BPM, as in FIG. 7, to roughly 30-BPM.

Figure 9:
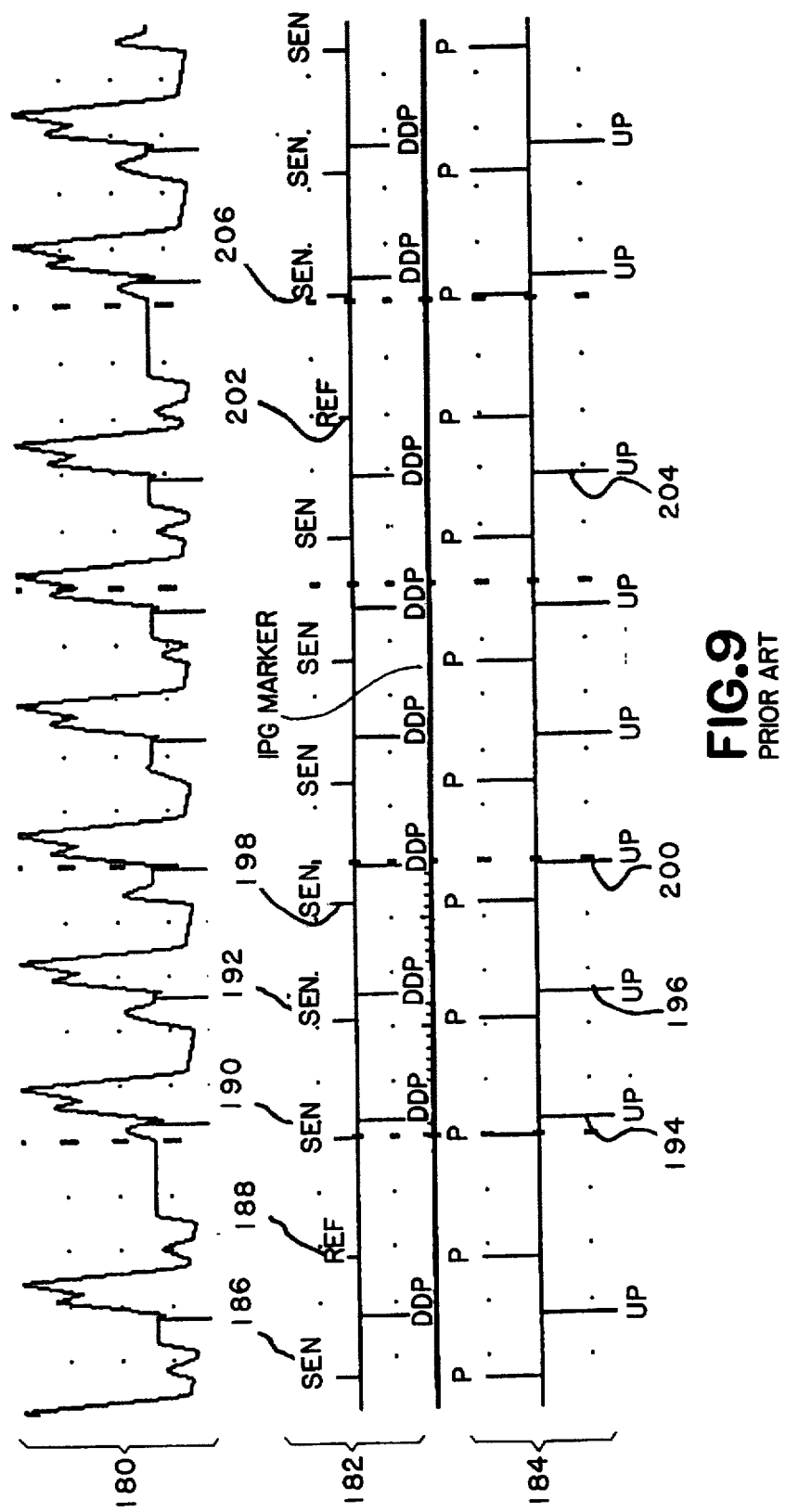
FIG. 9 is a plot of pulse generator and cardiac electrical activity illustrating Wenkebach-type operation of a prior art pulse generator in response to intrinsic atrial activity at a rate exceeding the pulse generator's upper rate limit.

In accordance with another aspect of the present invention, the rate smoothing function of pulse generator 10 as described herein can also smooth ventricular rate during Wenckebach operation. Those of ordinary skill in the art will appreciate that the effect of the rate smoothing function disclosed herein is similar to DDDR pacing with Wenckebach during activity. In FIG. 9, there is shown a strip-chart of cardiac and pulse generator activity during Wenkebach operation of a prior art (non-rate smoothing) pulse generator. In accordance with conventional practice, the pulse generator in FIG. 9 responds to intrinsic atrial activity at a rate exceeding the pulse generator's programmed upper rate limit by gradually extending the A-V delay between sensing atrial activity and delivery of ventricular pacing pulses.

In FIG. 9, the cardiac electrical waveform is designated with reference numeral 180, a marker channel diagram of sensed events is designated with reference numeral 182, and a marker channel diagram of paced events is designated with reference numeral 184. As shown in FIG. 9, atrial intrinsic events such as those designated with reference numerals 186, 188, 190, and 192, are occurring rapidly. In response to sensed atrial event 190, the prior art pulse generator delivers a ventricular pacing pulse 194 after a predetermined A-V delay period. However, another atrial event 192 is sensed soon thereafter, prior to the expiration of the pulse generator's lower rate limit escape interval. As a result, a resulting ventricular pulse 196 is delivered following an A-V delay that is extended with respect to that following atrial sense 190.

Similarly, a premature atrial sensed event 198 results in delivery of a ventricular pacing pulse 200, but only after expiration of an extended A-V delay that is longer than that following atrial event 192. This Wenkebach-like behavior of prior art pulse generators continues until an atrial event does not lead to delivery of a ventricular pulse as a result of it occurring during an atrial refractory period. In FIG. 9, atrial event 202 occurs during the refractory period initiated upon delivery of the prior ventricular pacing pulse 204. Thus, in accordance with conventional Wenckebach operation, no ventricular pulse is delivered prior to the occurrence of another atrial event 206. With atrial event 206, the process of gradually lengthening the A-V delay following rapid atrial events is repeated.

Figure 10:
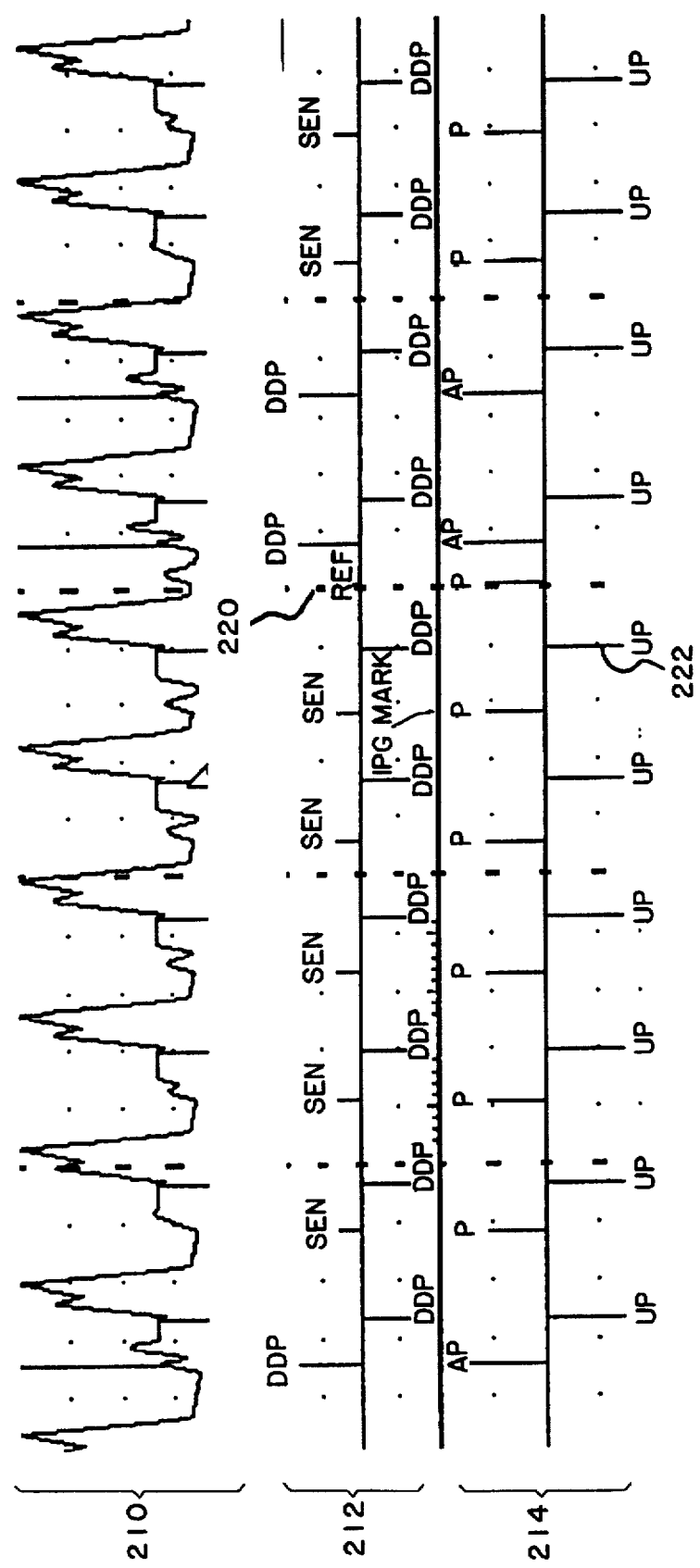
FIG. 10 is a plot of pulse generator and cardiac electrical activity illustrating the response of the pulse generator from FIG. 1 to intrinsic atrial activity at a rate exceeding the pulse generator's upper rate limit.

In FIG. 10 there is shown a strip chart of cardiac and pulse generator behavior for pulse generator 10 in accordance with the presently disclosed embodiment of the invention, showing the response of pulse generator 10 to the same series of rapid atrial events as from FIG. 9. In FIG. 10, the cardiac waveform is designated with reference numeral 210, a marker channel diagram of sensed events is designated with reference numeral 212, and a marker channel diagram of paced events is designated with reference numeral 214.

In FIG. 10 it can be seen that the rapid atrial rate causes the delay between delivery of ventricular pacing pulses to gradually increase until the atrial event designated with reference numeral 220 occurs during a refractory period initiated upon delivery of a previous ventricular pacing pulse 222.

Figure 11:
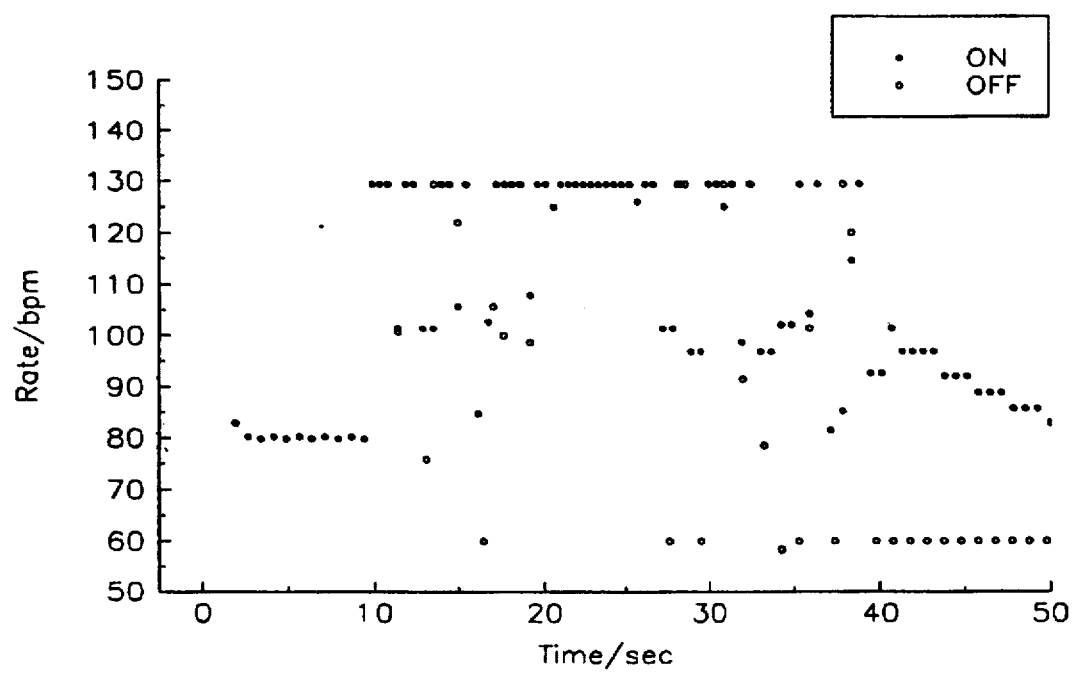
FIG. 11 is a plot showing the responses of a prior art pulse generator and the pulse generator from FIG. 1 to atrial fibrillation.

The rate smoothing capabilities of pulse generator 10 in accordance with the presently disclosed embodiment of the invention are also beneficial in preventing large ventricular rate variations during episodes of atrial tachycardia or atrial fibrillation. In FIG. 11 there is shown a plot of a ventricular pacing rate for a patient undergoing atrial fibrillation. The response of a prior art (non-rate smoothing) pulse generator is represented with open circles in FIG. 11, while the response of pulse generator 10 in accordance with the presently disclosed embodiment of the invention is represented with solid circles. As for the response of pulse generator 10 to intermittent loss of atrial sensing (see FIG. 7 and 8 above), pulse generator 10 in accordance with the present invention exhibits a response to atrial fibrillation in which the range of ventricular variation is narrowed as compared with the response of a prior art pulse generator.

The effect of rate smoothing is less notable than for previous atrial conditions described hereinabove, because intrinsic atrial activity is being tracked. However, those of ordinary skill in the art will observe that rate smoothing in accordance with the presently disclosed embodiment of the invention provides an incremental benefit by preventing the periodic large rate drops that can occur. Rate smoothing also allows the heart rate to gradually fall following an episode of atrial flutter.

The numeric parameters associated with the rate smoothing pulse generator function in accordance with the presently disclosed embodiment of the invention include: Rate Smoothing, which can be programmed to ON or OFF; Maximum Rate Drop, programmable to 1–20-BPM in 1 BPM increments; and Rate Smoothing Decay, programmable from 15-sec to 5-min. Several of the parameters described herein in connection with the rate smoothing function of pulse generator 10 are contemplated as being fixed at the time of manufacture or sale of the device (i.e., not physician programmable). These preferably nonprogrammable parameters would include: Rate Smoothing Threshold, which is preferably fixed at 31-mSec); and N and P, which are preferably fixed at 3 and 5, respectively. Setting P to 5 allows enough time to initiate the algorithm with confidence that Rate Smoothing operation should be performed. This value also allows Rate Smoothing to be initiated rapidly. Assuming that the value of P is 5, the value of N should be 3 to prevent the algorithm from triggering inappropriately when sporadic premature atrial contractions are present and, at the same time, is not so restrictive that Rate Smoothing is rarely initiated.

The Rate Smoothing Threshold parameter is preferably set to the value of DELTADEC (23 ms) plus one clock cycle. This prevents the dither of the Average Atrial Interval algorithm from erroneously initiating Rate Smoothing.

Figure 12A:
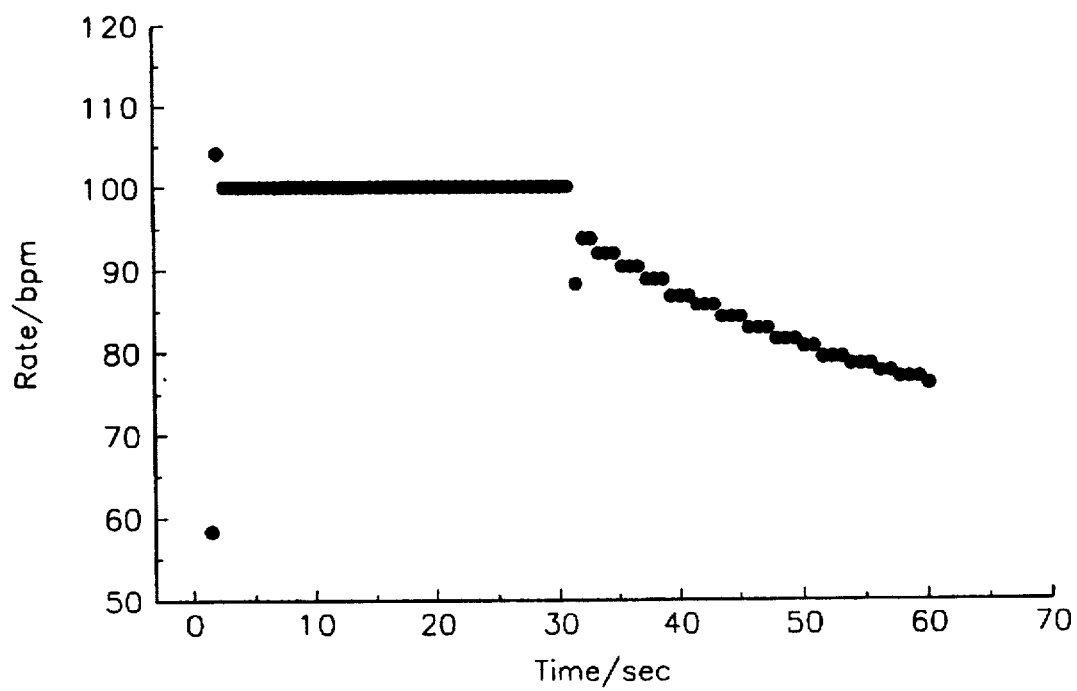
FIG. 12a is a plot showing the response of the pulse generator from FIG. 1 to a precipitous drop in atrial rate with a Maximum Rate Drop setting of 5-BPM.
Figure 12B:
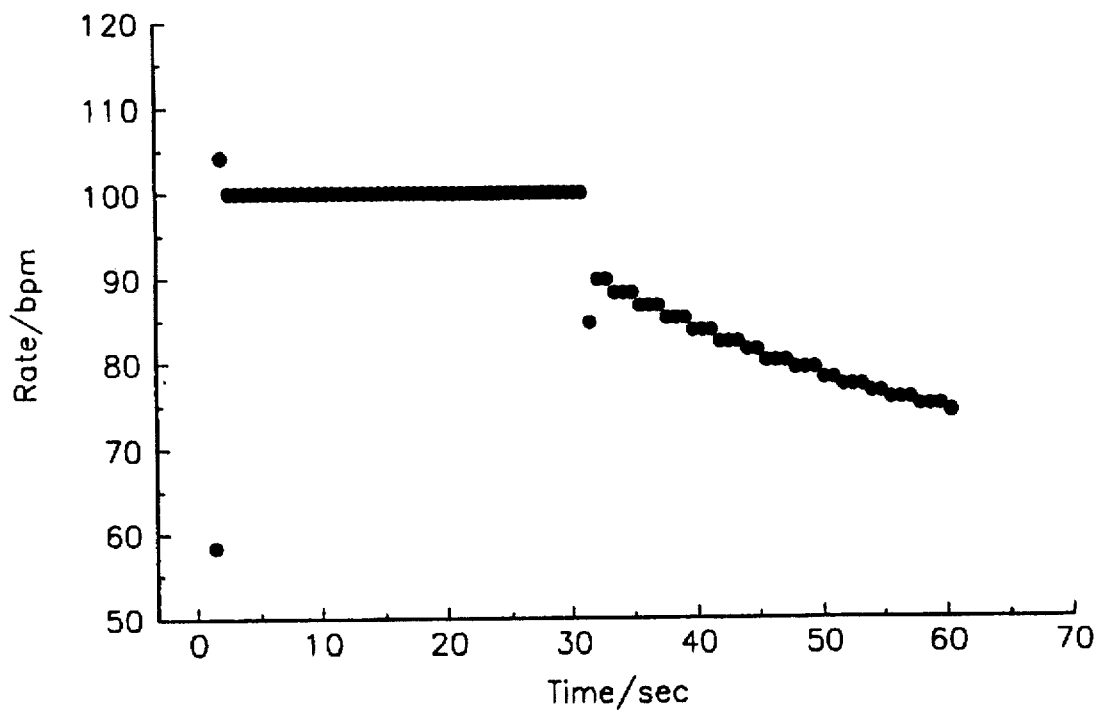
FIG. 12b is a plot showing the response of the pulse generator from FIG. 1 to a precipitous drop in atrial rate with a Maximum Rate Drop setting of 10-BPM.
Figure 12C:
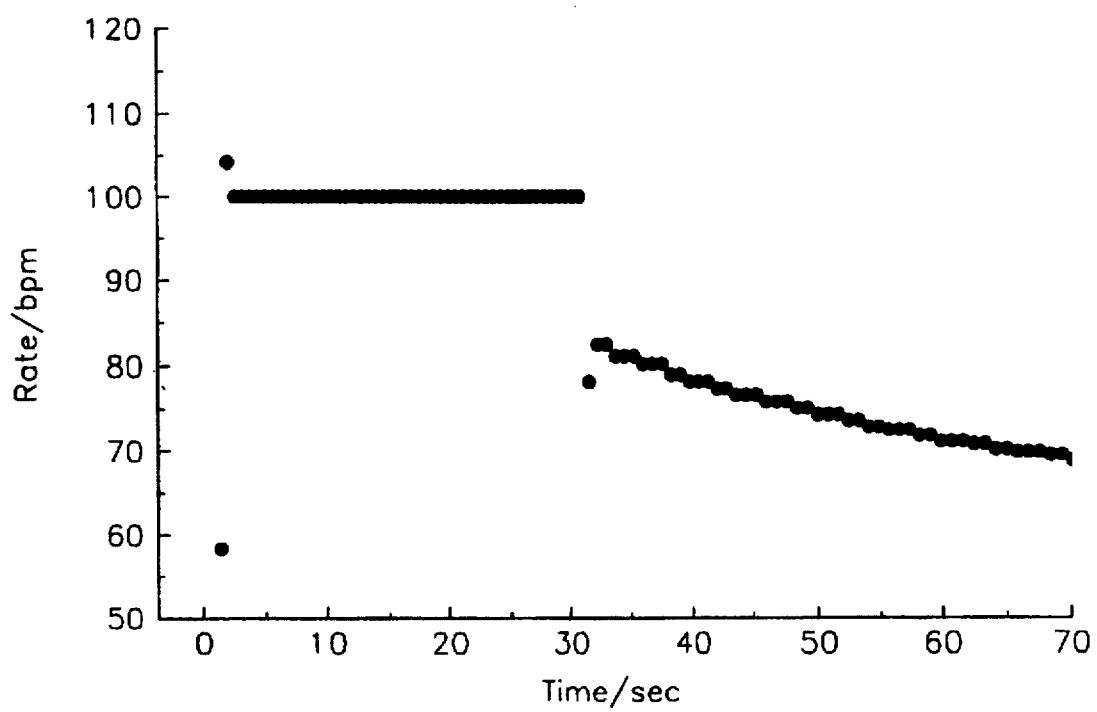
FIG. 12c is a plot showing the response of the pulse generator from FIG. 1 to a precipitous drop in atrial rate with a Maximum Rate Drop setting of 20-BPM.

The programmable parameters associated with the rate smoothing function described herein are preferably adjusted with the following information in mind: The Rate Smoothing Parameter is either ON or OFF. The Maximum Rate Drop should be set so that the patient's ventricular rate is not allowed to drop by large amounts on a beat-by-beat basis. FIGS. 12a, 12b, and 12c are plots showing the response of pulse generator 10 to a precipitous drop in atrial rate with Maximum Rate Drop settings of 5-, 10, and 20-BPM, respectively.

Figure 13:
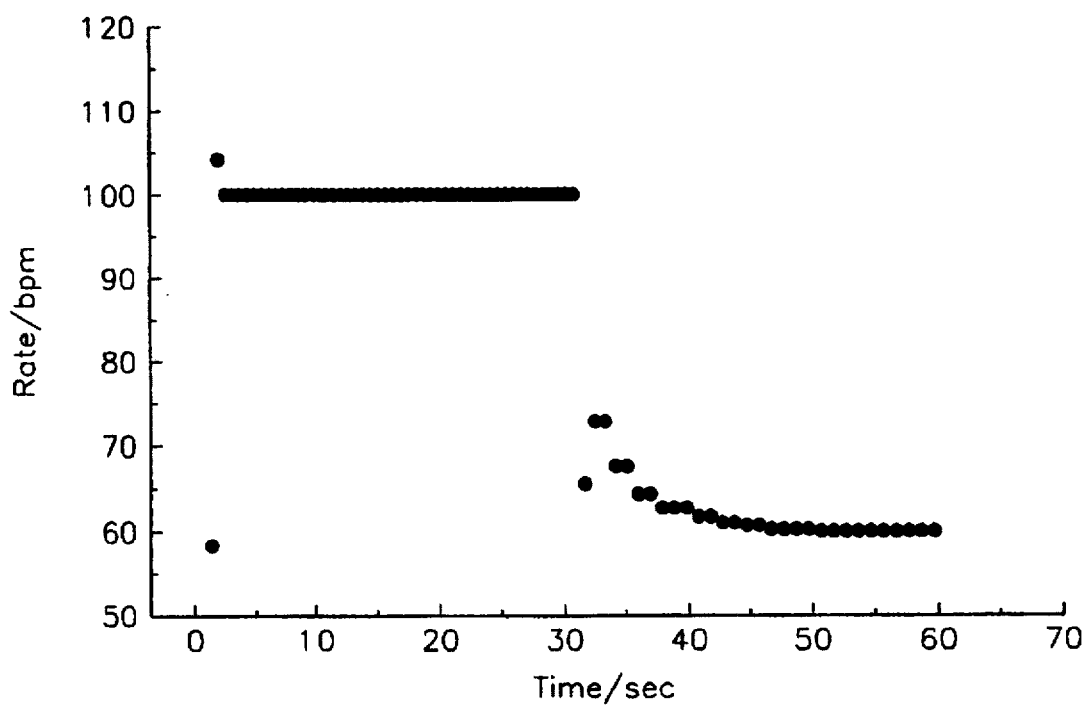
FIG. 13 is a plot showing the response of the pulse generator From FIG. 1 to a precipitous drop in atrial rate with a Rate Smoothing Decay setting of 10-sec.

As noted above, the Rate Smoothing Decay parameter controls the rate of decay of the smoothed pacing rate. A small value for this parameter can diminish the effectiveness of the rate smoothing function of pulse generator 10 since it allows for a more rapid decay. This may be desirable, however, for younger and more active patients who have rapid sinus rate swings. In FIG. 13 there is shown a plot similar to that from FIG. 12a, except that the Rate Smoothing Decay parameter for the plot of FIG. 13 has been changed from 120 seconds to 10 seconds. FIG. 13 illustrates that the short decay time overrides the effect of Maximum Rate Drop.

As previously suggested, it is contemplated that the rate smoothing functionality of pulse generator 10 as described herein may also be advantageously practiced in connection with cardioversion and defibrillation modes of pulse generator 10. For example, it is believed that the present invention may be advantageously practiced in conjunction with an implantable pulse generator/cardioverter/defibrillator (PCD), such as the Medtronic Model 7219 JEWEL™PCD, commercially available from the assignee of the present invention.

As will be appreciated by those of ordinary skill in the art, multi-function implantable devices, including PCDs, must be capable of discriminating between different types of arrhythmic or otherwise undesirable cardiac conditions, including bradycardia, tachycardia, and/or fibrillation, so that the device can apply a different appropriate therapy depending upon the condition detected. Such devices must also therefore be capable of switching between its various therapeutic modes in a manner which does not result in inappropriate treatment of a detected condition. For example, in U.S. Pat. No. 5,144,949 to Olson, entitled "Dual Chamber Rate Responsive Pacemaker With Automatic Mode Switching," there is described a rate-responsive pacemaker capable of automatically switching between the DDD mode, the VVIR mode, and the DDIR mode, depending upon the intrinsic cardiac activity that is detected. The Olson '949 patent is hereby incorporated by reference herein in its entirety.

In the foregoing description, the present invention has been described in connection with pulse generator 10 capable of operating in conventional pacing modes (e.g., DDD, DDDR, etc. . . . ) for the treatment of bradycardia. For the purposes of the following description, it will be assumed that pulse generator 10 is additionally operable in multiple modes, including a cardioverting mode and a defibrillation mode, and further that pulse generator 10 is capable of automatically switching between various therapeutic modes, in accordance, for example, with the teaching of the Olson '949 patent referenced in the previous paragraph.

Figure 14:
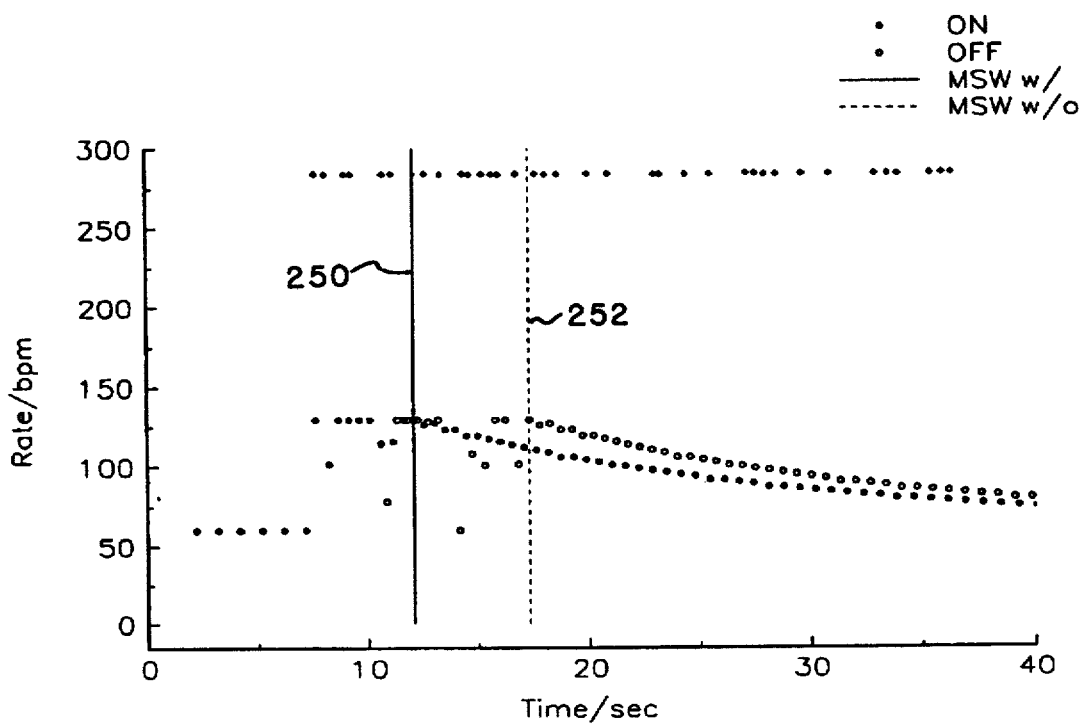
FIG. 14 is a plot showing the responses of a prior art pulse generator and the pulse generator from FIG. 1 to an episode of atrial fibrillation.

In FIG. 14, there is shown a plot of the response of a prior art pulse generator (hollow circles) and pulse generator 10 in accordance with the presently disclosed embodiment of the invention (solid circles) during an episode of atrial fibrillation. In FIG. 14, the diamonds indicate when atrial beats occur. Solid vertical line 250 in FIG. 14 corresponds to the point where pulse generator 10 in accordance with the presently disclosed embodiment of the invention undergoes a mode switch from pacing mode to defibrillation mode in response to the high and erratic atrial rate. Dashed vertical line 252 corresponds to the point where a prior art (i.e., non-rate smoothing) pulse generator undergoes this mode switch. FIG. 14 shows that rate smoothing shortens the time required for a multi-function device to undergo a mode switch.

Figure 15:
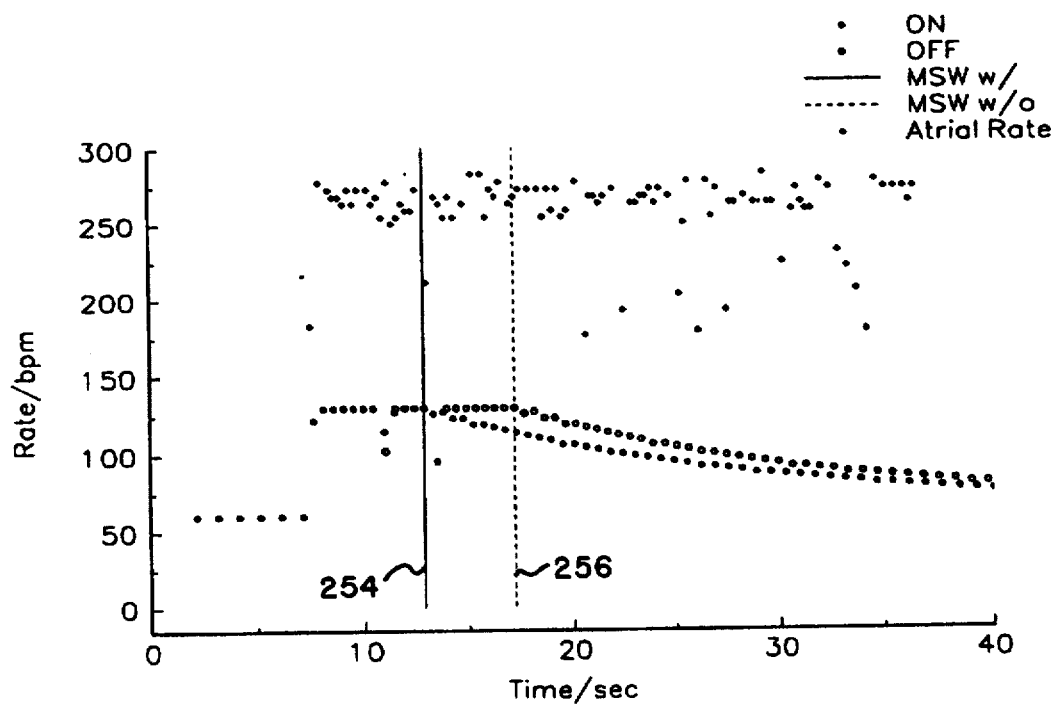
FIG. 15 is a plot showing the responses of a prior art pulse generator and the pulse generator from FIG. 1 to an episode of atrial flutter.

Similarly, FIG. 15 illustrates the responses of a prior art (i.e., non-rate smoothing) device (hollow circles) and pulse generator 10 in accordance with the presently disclosed embodiment of the invention (solid circles) to an episode of atrial flutter. As in FIG. 14, the diamonds in FIG. 15 indicate the occurrence of atrial beats. As with the responses to atrial fibrillation shown in FIG. 14, the responses depicted in FIG. 15 indicate that the mode switch from pacing mode to tachyarrhythmia mode occurs earlier for pulse generator 10 (solid line 254) than for a non-rate smoothing device (dashed line 256).

As illustrated in FIGS. 14 and 15, rate smoothing enhances the mode switching capabilities of pulse generator 10 due to the AAI algorithm described above. As noted above, the AAI is not allowed to exceed the pulse generator's escape interval. Since the rate smoothing function can decrease the escape interval, the AAI must be decreased also. This has the effect of speeding up the time to switch modes. Because AAI is forced to shorten, the rate-responsive A-V interval will shorten correspondingly.

Peak Rate Support Operation

As noted in the Summary of the Invention section above, in addition to the rate smoothing operation just described, pulse generator 10 in accordance with the present invention has a related Peak Rate Support capability intended to smooth out wide rate variations that are frequently observed in patients who are about to undergo an episode of Vaso-Vagal Syncope (VVS).

Like the rate smoothing function described above, the Peak Rate Support function of pulse generator 10 relies upon the maintenance of an AAI but could use some other indicator of current sensed atrial rate over the recent past. It is also used in the computation of an escape interval which determines when pacing pulses are delivered to the heart in the absence of sensed intrinsic cardiac activity.

The Peak Rate Support function of pulse generator 10 involves gradually reducing the pacing rate from a high intrinsic rate. In accordance with one aspect of the invention, the speed of this gradual reduction is set to be appropriate for the frequency of intrinsic heart rate oscillation to be suppressed.

It is contemplated that the Peak Rate Support function of pulse generator 10 may be operable in either of two modes: "triggered," or "always on." "Triggered" operation of the Peak Rate Support function involves a detection criteria for screening precipitous drops in intrinsic rate. "Always on" operation of the Peak Rate Support function does not require such detection criteria.

Regarding "triggered" operation, it is contemplated that the Peak Rate Support function can be implemented using any desired criteria. In one embodiment, the detection criteria is expressed in terms of the number of cardiac cycles which occur or, alternatively, the amount of time which elapses, as the patient's intrinsic rate drops from a predefined maximum rate to a predefined minimum rate. That is, such criteria would be fulfilled, for example, if the intrinsic rate falls from the predefined maximum rate to the predefined minimum rate within a certain number of beats, or within a certain period of time. An alternate could be the absolute value of the drop in rate over a given period of time. Other alternatives can include: disabling the trigger mechanism until the heart rate exceeds a given user-settable threshold, say 80 bpm; enabling PRS after exceeding such a threshold; enabling or triggering PRS if there is sufficient beat to beat variation for a given sequential number of beats; enabling PRS anytime the sensor rate exceeds a settable threshold; and so forth.

Whether "triggered" or "always on," Peak Rate Support intervention involves two modes of operation: track mode and decay mode. In both track mode and decay mode, the Peak Rate Support function specifies how the pulse generator's escape interval—the current pacing interval to be used in the absence of intrinsic activity—is updated each time the AAI is computed.

In track mode, the Peak Rate Support (PRS) function attempts to keep the escape rate as close to the intrinsic rate as possible without allowing the escape rate to overshoot the intrinsic rate. In the preferred embodiment the AAI value is updated as described in the description of the rate smoothing function above, whereby a new escape interval is calculated. The track mode escape interval calculation is summarized in the following Table 1, wherein: "A-A interval" refers to the current intrinsic atrial interval; "AAInew" refers to the newly calculated AAI interval; "AAIold" refers to the previous AAI; and "Escape Interval" refers to the current pacing interval. [Note that the conditions A and C are mutually exclusive]

TABLE 1

| CONDITION | NEW ESCAPE INTERVAL | NEW OPERATION |
|---|---|---|
| (A) AAInew > A-A interval | Escape Interval = AAInew | Remain in Track Mode |
| (B) AAIold > A-A interval and AAInew ≦ A-A interval | No change to current Escape Interval | Remain in Track Mode |
| (C) AAIold ≦ A-A interval and AAInew ≦ A-A interval | Escape Interval = AAInew | Go to Decay Mode |

As set forth in Table 1, when the intrinsic rate drops below AAI and the newly adjusted AAI (indicating a change in the sinus rate greater than the speed with which AAI adjusts), the Peak Rate Support function moves into Decay Mode. In Decay mode, escape interval calculation, performed each time the AAI is updated, is performed according to the following Table 2, wherein: "#Beats" refers to a count value that is reset each time an adjustment is made to the Escape Interval; "Decay Interval" refers to the millisecond adjustment that is made to the Escape Interval in Decay Mode; and "Decay Beats" refers to the number of cardiac cycles between Escape Interval adjustments.

"Decay Beats" cardiac cycles, until intrinsic activity resumes. When intrinsic activity produces a change in the AAI and is also greater than the AAI, the Escape Interval begins to adjust to the intrinsic rhythm, then returning to Track Mode.

Figure 16:
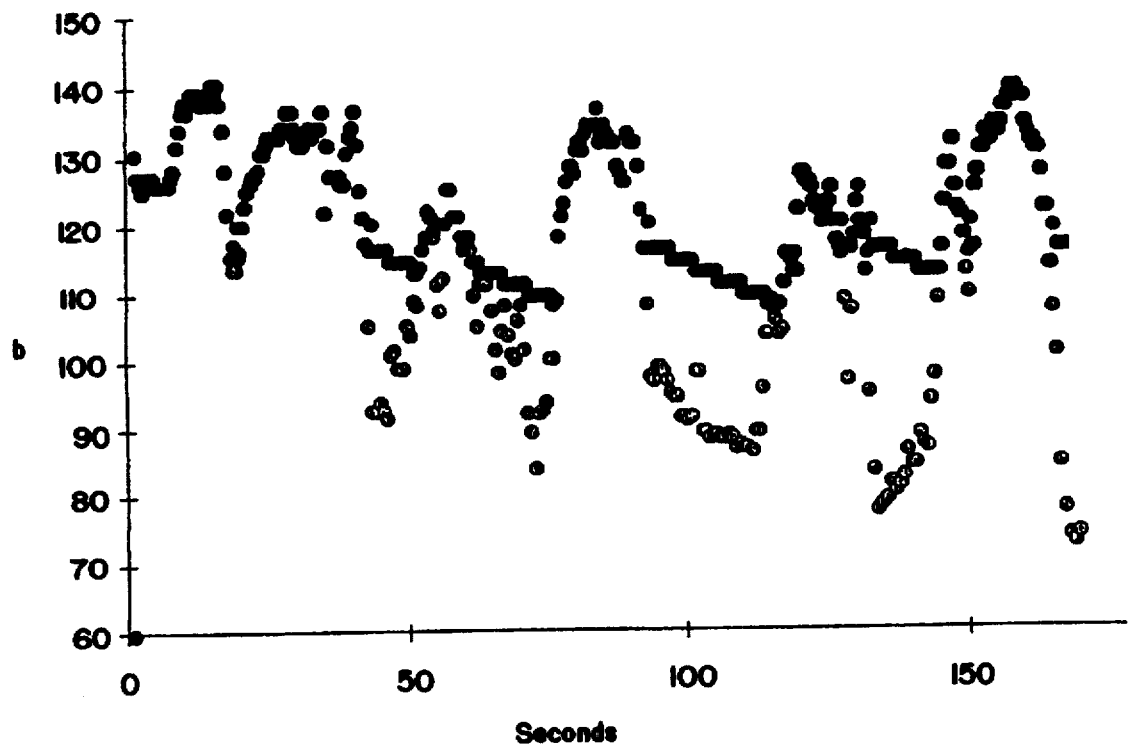
FIG. 16 is a plot showing the response of the pulse generator from FIG. 1 operating with its peak rate support function in accordance with one embodiment of the invention.

A plot illustrating the operation of the Peak Rate Support function in accordance with the present invention is shown in FIG. 16. In FIG. 16, the lighter dam points reflect the intrinsic atrial activity of a patient, which can be observed to fluctuate abruptly over a relatively wide range of atrial rates. A conventional atrial-synchronous pacemaker would undesirably track the intrinsic atrial rate, thus leading to correspondingly large fluctuations in delivered pacing pulses. The darker data points in FIG. 16, however, reflect the response of a pacemaker in accordance with the present invention having a Peak Rate Support function intended to limit the occurrences of abrupt drops in rate of delivery of pacing pulses, as previously described with reference to Tables 1 and 2. In FIG. 16 it can be observed that despite the abrupt drops in intrinsic atrial rate, the rate of delivery of stimulating pulses is substantially less erratic. FIG. 16 shows how the Peak Rate Support function causes the pacing rate to be gradually, rather than quickly, reduced.

With a peak rate support function available, some other therapy options may be pursued. First, the use of the PRS function can be monitored and if it is activated more than some predetermined amount, a change or elevating in therapy can be implemented and executed.

For example, if the number of times PRS decay state is changed within a range of time (over several minutes, for example) exceeds an expected or acceptable amount which is preprogrammed, then an unstable atrial rate is implicated. Such patterns have been witnessed in VV Syncope patients prior to a syncopal episode. Therefore the pacer that could use this information to implement elevated pacing or to raise the lower rate for a time period setable by an attending physician would be advantageous.

Another example would be to use the monitoring of PRS decay for a drop in pacing rate that starts above a settable threshold and continues to require PRS functional smoothing for more than another settable drop, say 20 beats per minute. This also would indicate a VVS episode and suggest

TABLE 2

| | CONDITION | NEW ESCAPE INTERVAL | NEW OPERATION | NEW #BEATS |
|---|---|---|---|---|
| L | #Beats = Decay Beats and no intrinsic atrial activity | Escape Interval = Escape Interval + Decay Interval | Remain in Decay Mode | 0 |
| M | #Beats < Decay Beats and no intrinsic atrial activity | No change to current Escape Interval | Remain in Decay Mode | #Beats + 1 |
| N | A-A interval ends with intrinsic activity ≧ AAInew and #Beats = Decay Beats | Escape Interval = Escape Interval + Decay Interval | Remain in Decay Mode | 0 |
| O | A-A interval ends with intrinsic activity ≧ AAInew and #Beats < Decay Beats | No change to current Escape Interval | Remain in Decay Mode | #Beats + 1 |
| P | A-A interval ends with intrinsic activity < AAInew | Escape Interval = AAInew | Go to Track Mode | 0 |

Once in the Decay Mode, a different set of rules applies to the calculation of Escape Interval, as set forth in Table 2 above. The Escape Interval will continue to increase every alternative or adjunct therapies be implemented. (Other therapies could include drugs, neural (stimulation, raising pacing rate, activating an implemented drug pump, other timing changes, etc.) all of which can be controlled by the physician once the monitoring of PRS decay function provides such an indication. Many alternative methods for notifying a user are possible and none should be excluded, including feedback during periodic monitoring, direct warnings to the patient, and so forth.

An additional feature of the PRS function is to hold a maximum heart rate. If the PRS algorithm was tuned so the decay beats following an escape interval shortening was very long, then the algorithm would resemble a ratchet—one can raise the rate up, but it would not go down. This may have benefit for patients with sick sinus post-exercise when they experience pauses. To modify PRS to behave so, one can either make the decay beats very long, or the first time into the decay state use along decay beat and after that use a shorter number so the device returned to lower rate faster. Table 1, when it says "Go to Decay" can they also say "Reset Decay Beats to 200". Then transitions in Table 2 "L" should say decay beats=4 or some other conventional amount.

Coordination of Smoothing and Support Operations

It should be noted that several supporting processes have been described to accomplish both rate smoothing and peak rate support. Both these features accomplish the enhancement of pacing by allowing the patient's heart rate to climb quickly but not drop quickly.

The supporting processes include 1) maintaining an AM by increasing relatively quickly or decreasing relatively slowly its value based only on certain measured atrial depolarization timings.

and, 2) an N of P criteria used to avoid situations where only a few aberrant pulses might otherwise set rate smoothing or support into action.

Many of the criteria in these support processes can be set at the factory or by the attending physician to vary the manner in which the device is responsive. Clearly variations on the combining of these support process and features will occur to the reader without leaving the fair ambit of this invention.

From the foregoing detailed description of a specific embodiment of the invention, it should be apparent that a pulse generator having enhanced rate smoothing and peak rate support capabilities has been disclosed. Although a specific embodiment of the invention has been described herein in detail, this is merely to illustrate the invention in various of its aspects, and is not intended to be limiting with respect to the scope of the invention.

It is contemplated that various substitutions, alterations, and/or modifications, including but not limited to those implementation variations and options specifically discussed herein, may be made to the disclosed embodiment without departing from the spirit and scope of the invention as defined in the appended claims, which follow. For example, although the present invention has been described herein primarily in the context of a cardiac pulse generator, it is believed that the invention may be advantageously practiced in connection with other implantable devices, including (as noted above with reference to the interaction of the disclosed rate smoothing functions with mode switching in a multi-mode PCD) a multi-function pulse generator/cardioverter/defibrillator.

What is claimed is:

1. A cardiac pulse delivery and sensing apparatus comprising:

a housing adapted to be implanted in an individual said housing containing means for generating and delivering stimulating pulses to an electrical connection outside said housing said electrical connection arranged and disposed for electrical connection to sensing and stimulating pulse delivery lead means and wherein said lead mean are configured and designed to allow for implantation so as to be in close association with said individual's heart so as to provide electrical connection between said heart and said electrical connection, a timing and control processor circuit and a memory circuit within said housing having control of the timing of delivery of said stimulating pulses and for timing said sensed heart signals and for storing values related to such timing in an associated portion of said memory circuit and wherein said processor circuit comprises as least two processors; a rate smoothing determining processor for determining whether rate smoothing criteria are met in sensed signals from said heart when a rapid rate drop is detected and; a rate support determining processor for determining from said values related to such timing when to maintain a support rate, said maintenance of support rate processor having two modes, a tracking mode which follows an intrinsic atrial rate and a decay mode which allows the support rate to fall in a controlled manner and wherein said timing and control processor circuit also comprises circuit means for adjusting the timing of said stimulating pulses in response to said rate smoothing processor and rate support processor's determining.

2. An apparatus as set forth in claim 1 wherein said rate smoothing determining processor bases its determination on a current Averaged Atrial Interval (AAI) value stored and updated in said memory circuit in which value is the measure of a previous AAI summed with a value for an increment of time or decremented by a value for a decrement of time such that:

a) said previous AAI is incremented by a positive increment interval when the time between the last pair of atrial sensed events or the time between a leading sensed atrial event and a paced atrial event or the time between the last two atrial paced events is less than the value of the previous AAI, but b) said previous AAI is decremented by a negative increment interval when the time between the last pair of atrial sensed events or the time between a leading sensed atrial event and a paced atrial event or the time between the last two atrial paced events is greater than the value of the previous AAI;

such that if the current AAI is less than the value of the previous AAI minus a predetermined Maximum Rate Drop interval value, then an indicator value in a memory circuit in favor of rate smoothing is "set".

3. An apparatus as set forth in claim 2 wherein when said indicator "Count N" is set in favor of rate smoothing and a next indicator value in said memory circuit will be either: "set" depending on if the current AAI is less than the value of the previous AAI minus said predetermined Maximum Rate Drop interval value; and "not-set" if not and wherein a set of all previously set or not-set indicator values is used by said rate smoothing determining circuit to determine whether or not to initiate rate smoothing.

4. An apparatus as set forth in claim 3 wherein the set of indicators available to be put into either said set or not-set condition is equal to a number P, said number P being a variable representing a number of memory circuit elements in said memory circuit that can be used for storing said set or not set variables and an index "CountP" is set equal to the variable from 1 to P that is being considered, and when the value of the index CountP=P, the next variable to be set or reset is indexed by CountP=1.

5. An apparatus as set forth in claim 2 wherein when said indicator is set a next indicator will be either: "set" depending on if the current AAI is less than the value of the previous AAI minus said predetermined Maximum Rate Drop interval value; and "not-set" if not and wherein the total of all previously set indicator values is determined and said total is compared by said rate smoothing determining circuit to a predetermined number N stored in said memory circuit and if said total is determined to be greater or equal to N, then said rate smoothing determining circuit signals said timing and control circuit to initiate rate smoothing.

6. An apparatus as set forth in claim 5 wherein the number N is predetermined by a user and stored by that user into said memory circuit for storing N's value.

7. An apparatus as set forth in claim 2 wherein the rate smoothing is accomplished by said rate smoothing processor accomplishing the summing of the current AAI with a small additional increment to reach the next AAI.

8. An apparatus as set forth in claim 7 wherein said small additional increment size is a storable value set by a user and stored by that user into said memory circuit for storing said additional increment's size value by use of a device that can communicate with said apparatus.

9. Apparatus as set forth in claim 1 wherein said timing and control processor circuit can be controlled by reference to a value by either said rate smoothing determining processor or by said rate support determining processor or by both processors depending on the value which is set by a user and stored by that user into said memory circuit.

10. Apparatus as set forth in claim 1 wherein said timing and control processor circuit is controlled by both said rate smoothing determining processor and by said rate support determining processor.

11. Apparatus as set forth in claim 9 wherein said rate support determining processor supports PRS and wherein said rate support processor is only activated upon achievement of a predetermined criterion.

12. Apparatus as set forth in claim 9 wherein said rate support determining processor supports PRS and wherein when said rate support processor is activated in accord with preset criteria, said activation causes an indication of said meeting of such criterion to be reported to the user.

13. A cardiac pulse delivery and sensing apparatus comprising:

a housing adapted to be implanted in an individual said housing containing means for generating and delivering stimulating pulses to an electrical connection outside said housing said electrical connection arranged and disposed for electrical connection to sensing and pulse delivery leads connected thereto and wherein said leads are configured and designed to allow for implantation so as to be in close association with said individual's heart so as to provide electrical connection between said heart and said electrical connection, a timing and control processor circuit and a memory circuit within said housing having control of the timing of delivery of said stimulating pulses and for timing said sensed heart signals and for storing values related to such timing in an associated portion of said memory circuit wherein said processor circuit comprises; a rate smoothing determining processor for determining whether rate smoothing criteria are met in sensed signals from said heart if a rapid rate drop is detected; and wherein said processor circuit also comprises circuit means for adjusting the timing of said stimulating pulses in response to said determination so as to allow said drop to occur in a smoothed manner without first raising a pacing rate to a predetermined rate.

14. A cardiac pulse delivery and sensing apparatus comprising:

a housing adapted to be implanted in an individual said housing containing means for generating and delivering stimulating pulses to an electrical connection outside said housing said electrical connection arranged and disposed for electrical connection to sensing and pulse delivery leads connected thereto and wherein said lead are configured and designed to allow for implantation so as to be in close association with said individual's heart so as to provide electrical connection between said heart and said electrical connection, a timing and control processor circuit and a memory circuit means within said housing having control of the timing of delivery of said stimulating pulses, for timing said sensed heart signals and for storing values related to such timing in an associated portion of said memory circuit means and wherein said processor circuit comprises; a rate support determining processor for determining from said stored values when to maintain a support rate so as to prevent rapid rate drops; and wherein said processor circuit also comprises circuit means for adjusting the timing of said stimulating pulses in response to said determination, said support rate processor having two modes, a tracking mode which follows an intrinsic atrial rate and a decay mode which allows the support rate to fall in a controlled manner.

15. Apparatus as set forth in claim 14, said timing and control circuit further comprising a sensor and a rate drop determination circuit, wherein the rate support determining processor is only triggered by said sensor and rate drop determination circuit and wherein said rate drop determination circuit determines based on sensed depolarizations that an occurrence of a drop in intrinsic rate from a predetermined maximum to a predetermined minimum within a given period has occurred.

16. Apparatus as set forth in claim 14, said timing and control circuit further comprising a sensor and a rate drop determination circuit, wherein the rate support determining processor is only triggered by said sensor and rate drop determination circuit that determines based on sensed depolarizations that an occurrence of a drop in intrinsic rate by a predetermined absolute value over a given time period has occurred.

17. Apparatus as set forth in claim 14, said timing and control circuit further comprising a sensor and a rate drop determination circuit, wherein the rate support determining processor is triggered by triggered by said sensor and rate drop determination circuit that determines based on sensed depolarizations that an occurrence of a predefined drop in the intrinsic rate over a given period has occurred.

18. Apparatus as set forth in claim 14 wherein said timing and control circuit retains timing values of escape intervals, including a present and a previous escape interval, and wherein when the rate support determining processor is on, said timing and control circuit functions by increasing an escape interval to slow pacing from one paced beat to the next, but does not function to slow pacing during "decay beats" while in said decay mode, the number of said decay beats being determined by whether an intrinsic event is found within said previous escape interval.

19. A method for timing and controlling the delivery of pacing pulses to a heart comprising one step from the following set of steps, a, b, and c:

a) 1) monitoring and detecting occurrences of rapid rate drop
   2) when a rapid heart rate is detected, enabling a processor to apply smoothing criteria to the timing of delivery of subsequent pacing pulses,
b) 1) monitoring and detecting occurrences of wide variation in heart rate,
   2) enabling a processor to apply rate support criteria to subsequent pacing pulses following the detection of an occurrence of wide rate variation, and
c) 1) monitoring and detecting occurrences of rapid rate drop and wide variation in intrinsic heart rate
   2) when a rapid heart rate drop or occurrence of wide rate variation is detected, enabling a processor to apply a combination of rate support and rate smoothing criteria to the timing and delivery of subsequent pacing pulses.

20. A method for timing and controlling the delivery of pacing pulses to a heart comprising:

monitoring and detecting occurrences of rapid rate drop when an intrinsic rapid heart rate drop is detected, enabling a processor to apply smoothing criteria to the timing of delivery of subsequent pacing pulses such that an intrinsic rapid rate drop is not allowed to occur but instead a smoothed rate drop is supported by said timing.

21. A method for timing and controlling the delivery of pacing pulses to a heart comprising:

monitoring and detecting occurrences of wide variation in heart rate when an occurrence of wide variation in heart rate is detected, enabling a processor to apply rate support criteria to the timing of delivery of subsequent pacing pulses such that the paced patient's intrinsic rate is not allowed to fall by adjusting the timing of pacing pulse delivery downward no faster than extinction of a timed interval adjusted by said processor to reflect the amount of rate support needed so said interval is directly proportional in size to the amount of support determined by said processor to be needed.

* * * * *